US 9,308,321 B2

(12) United States Patent
Alderete, Jr. et al.

(10) Patent No.: US 9,308,321 B2
(45) Date of Patent: Apr. 12, 2016

(54) INFUSION DEVICE HAVING GEAR ASSEMBLY INITIALIZATION

(71) Applicant: MEDTRONIC MINIMED, INC., Northridge, CA (US)

(72) Inventors: Juan M. Alderete, Jr., Granada Hills, CA (US); Salman Monirabbasi, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 565 days.

(21) Appl. No.: 13/769,766

(22) Filed: Feb. 18, 2013

(65) Prior Publication Data

US 2014/0236087 A1    Aug. 21, 2014

(51) Int. Cl.
*A61M 1/00* (2006.01)
*A61M 5/145* (2006.01)

(52) U.S. Cl.
CPC ......... *A61M 5/1452* (2013.01); *A61M 5/14566* (2013.01)

(58) Field of Classification Search
CPC .................. A61M 5/1454; A61M 5/14566
USPC ............................................. 604/152
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic Minimed, Inc.

(Continued)

*Primary Examiner* — Edelmira Bosques
*Assistant Examiner* — Leah Swanson
(74) *Attorney, Agent, or Firm* — Ingrassia Fisher & Lorenz, P.C.

(57) ABSTRACT

Apparatus are provided for infusion devices and related operating methods. An exemplary infusion device includes a housing to receive a shaft coupled to a plunger disposed in a reservoir and a gear assembly including a first gear to engage the shaft, wherein the first gear exhibits rotational freedom in a direction opposite a delivery direction. One exemplary method of operating the infusion device comprises identifying a reset condition and in response to the reset condition, operating a motor having a rotor coupled to the gear assembly to provide the rotational freedom for the first gear.

23 Claims, 14 Drawing Sheets

(56) References Cited

U.S. PATENT DOCUMENTS

| | | |
|---|---|---|
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |

(56) References Cited

U.S. PATENT DOCUMENTS

| | | |
|---|---|---|
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,621,893 B2 | 11/2009 | Moberg et al. |
| 7,828,764 B2 | 11/2010 | Moberg et al. |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0051711 A1* | 2/2008 | Mounce .............. A61J 1/1406 604/131 |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2011/0160666 A1* | 6/2011 | Hanson .............. A61M 5/14248 604/151 |
| 2011/0233393 A1 | 9/2011 | Hanson et al. |
| 2012/0165733 A1 | 6/2012 | Bazargan et al. |
| 2012/0259282 A1 | 10/2012 | Alderete, Jr. et al. |
| 2013/0184638 A1* | 7/2013 | Scarpaci .............. G01V 8/20 604/28 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO2009/102355 A2 | 8/2009 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
(MiniMed, 1996). The MiniMed 506. 7 pages. Retrieved on Sep. 16, 2003 from the World Wide Web: http://web.archive.org/web/19961111054527/www.minimed.com/files/506_pic.htm.

(56) References Cited

OTHER PUBLICATIONS (MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.

Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Inlayer Coating," Analytical Chemistry, vol. 65, No. 15, Aug. 1, 1993, pp. 2072-2077.
Nakamoto, S., et al., "A Lift-Off Method for Patteming Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artiffical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

(56) References Cited

OTHER PUBLICATIONS

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

Jacques L. Favreau, Dynamic Pulse-Width Modulation Motor Control and Medical Device Incorporating Same, U.S. Appl. No. 13/425,174, filed Mar. 20, 2012.

Jacques L. Favreau, Occlusion Detection Using Pulse-Width Modulation and Medical Device Incorporating Same, U.S. Appl. No. 13/425,180, filed Mar. 20, 2012.

Jacques L. Favreau, Motor Health Monitoring and Medical Device Incorporating Same, U.S. Appl. No. 13/425,190, filed Mar. 20, 2012.

\* cited by examiner

INFUSION DEVICE HAVING GEAR ASSEMBLY INITIALIZATION

TECHNICAL FIELD

Embodiments of the subject matter described herein relate generally to medical devices, and more particularly, embodiments of the subject matter relate to resetting or otherwise initializing a gear assembly that is configured to engage the shaft of a plunger in a fluid infusion device.

BACKGROUND

Infusion pump devices and systems are relatively well-known in the medical devices, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Some fluid infusion devices also include a force sensor designed to detect and indicate a pump malfunction and/or non-delivery of the medication to the patient due to a fluid path occlusion.

In some fluid infusion devices, the reservoir may be removed or replaced by a user, for example, to replace an empty reservoir with a new reservoir. Accordingly, it is desirable to provide a fluid infusion device that accommodates the insertion and removal of the reservoir in a manner that avoids inadvertent fluid delivery or potential damage to the drive system when engaging and/or disengaging the reservoir with the drive system.

BRIEF SUMMARY

An embodiment of an infusion device is provided. The infusion device includes a housing to receive a shaft coupled to a plunger disposed in a reservoir and a gear assembly including a gear configured to engage the shaft when the reservoir is inserted in the housing. The gear exhibits rotational freedom in a direction opposite a delivery direction.

In one embodiment, an infusion device includes a housing to receive a shaft coupled to a plunger disposed in a reservoir, a gear assembly including a gear configured to engage the shaft, a motor having a rotor coupled to the gear assembly, and a control module coupled to the motor. The control module operates the motor to provide rotational freedom for the gear in a direction opposite a delivery direction for the plunger in response to a reset condition.

In another embodiment, an infusion device includes a housing to receive a shaft coupled to a plunger of a reservoir, a gear assembly including a gear configured to engage the shaft when the reservoir is inserted in the housing, and a mechanical element coupled to the gear. The mechanical element applies a force that results in the gear exhibiting rotational freedom in a direction opposite a delivery direction of the plunger when the reservoir is not inserted in the housing or the shaft is otherwise disengaged with the gear.

In yet another embodiment, a method is provided for operating an infusion device. The infusion device includes a gear assembly including a gear configured to engage a shaft coupled to a plunger of a reservoir such that rotation of the gear in a first direction results in displacement of the plunger in a delivery direction to deliver fluid from the reservoir. The method involves identifying a reset condition, and in response to the reset condition, operating a motor having a rotor coupled to the gear assembly to provide rotational freedom for the gear in a second direction opposite the first direction.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and not necessarily drawn to scale.

DETAILED DESCRIPTION

Figure 1:
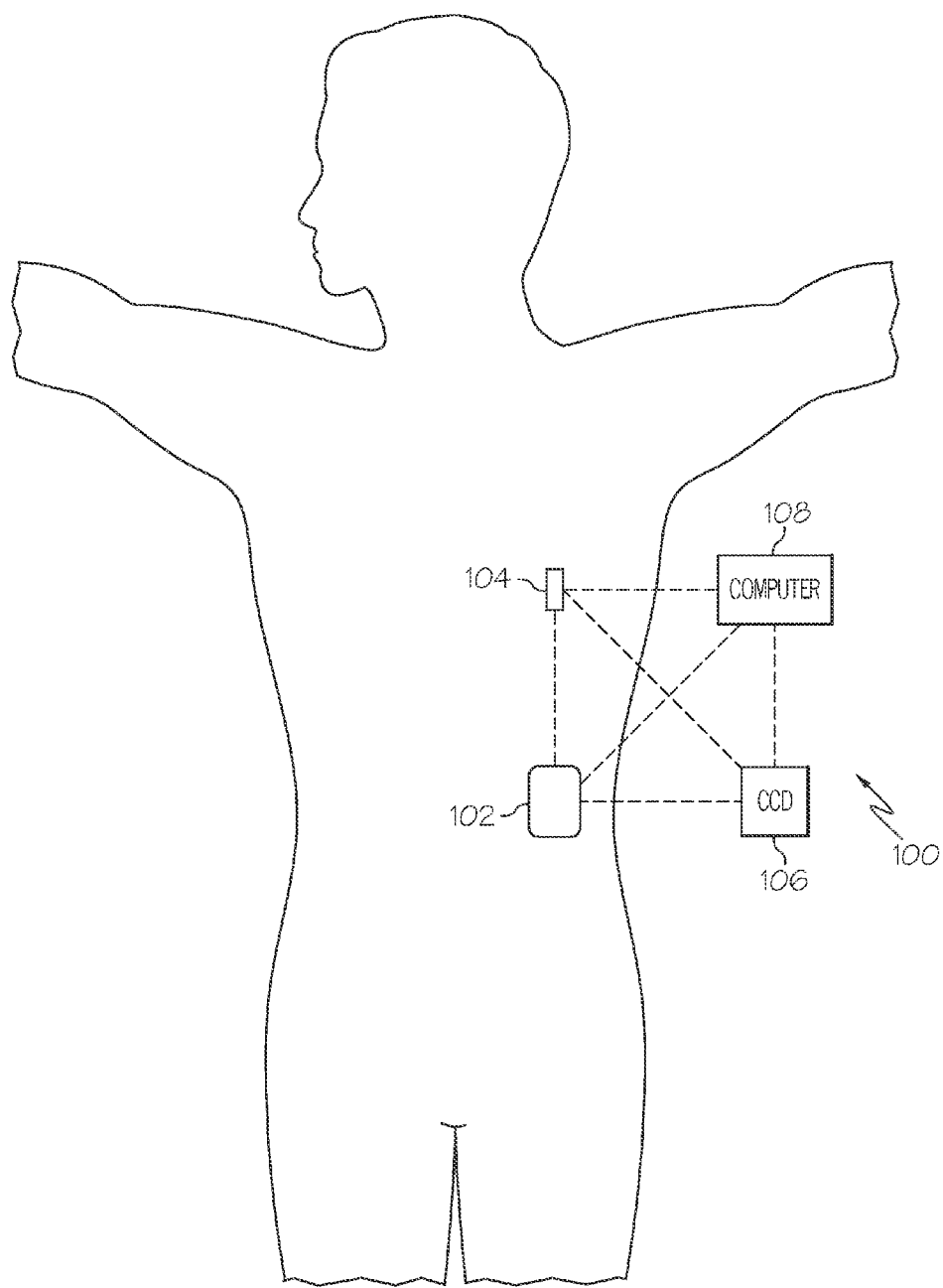
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Embodiments of the subject matter described herein generally relate to fluid infusion devices that accommodate insertion of a fluid reservoir with reduced likelihood of inadvertent fluid delivery from the reservoir. As described in greater detail below, the gear assembly that engages the shaft of the reservoir is configured in a state in which the gear that engages the shaft has rotational freedom in the direction opposite the direction in which the gear rotates to deliver fluid from the reservoir. As a result, the gear exhibits slack that allows the shaft of the reservoir to be engaged with the gear without inadvertently displacing the plunger into the barrel of the reservoir. As used herein, any rotation or displacement of gears or other components described as being in the "fluid delivery direction" or "positive delivery direction" should be understood referring to as rotation or displacement of that respective gear or component that is in the same direction in which that respective gear or component rotates or is displaced to produce displacement of the plunger into the barrel of the reservoir. Conversely, any rotation or displacement of gears or other components described as being in the "negative delivery direction" should be understood referring to as rotation or displacement of that respective gear or component that is in the direction opposite that in which that respective gear or component rotates or is displaced to produce displacement of the plunger into the barrel of the reservoir. Thus, the "negative delivery direction" is opposite the "fluid delivery direction" or "positive delivery direction."

While the subject matter described herein can be implemented in any electronic device that includes a displaceable shaft coupled to a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893 which are herein incorporated by reference.

Turning now to FIG. 1, in exemplary embodiments, an infusion system 100 includes, without limitation, a fluid infusion device (or infusion pump) 102, a sensing arrangement 104, a command control device (CCD) 106, and a computer 108. The components of an infusion system may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049, 803, assigned to the assignee of the present application, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like. The sensing arrangement 104 generally represents the components of the infusion system 100 configured to sense a condition of the user, and may include a sensor, a monitor, or the like, for providing data indicative of the condition that is sensed and/or monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

In various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in various embodiments, the CCD 106 and/or the computer 108 include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 may utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, and 7,323,142, all of which are incorporated herein by reference in their entirety. In such embodiments, the sensing arrangement 104 is configured to sense a condition of the user, such as, blood glucose level or the like. The infusion device 102 may be configured to deliver fluid in response to the condition sensed by the sensing arrangement 104. In turn, the sensing arrangement 104 may continue to sense a new condition of the user, allowing the infusion device 102 to deliver fluid continuously in response to the new condition sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
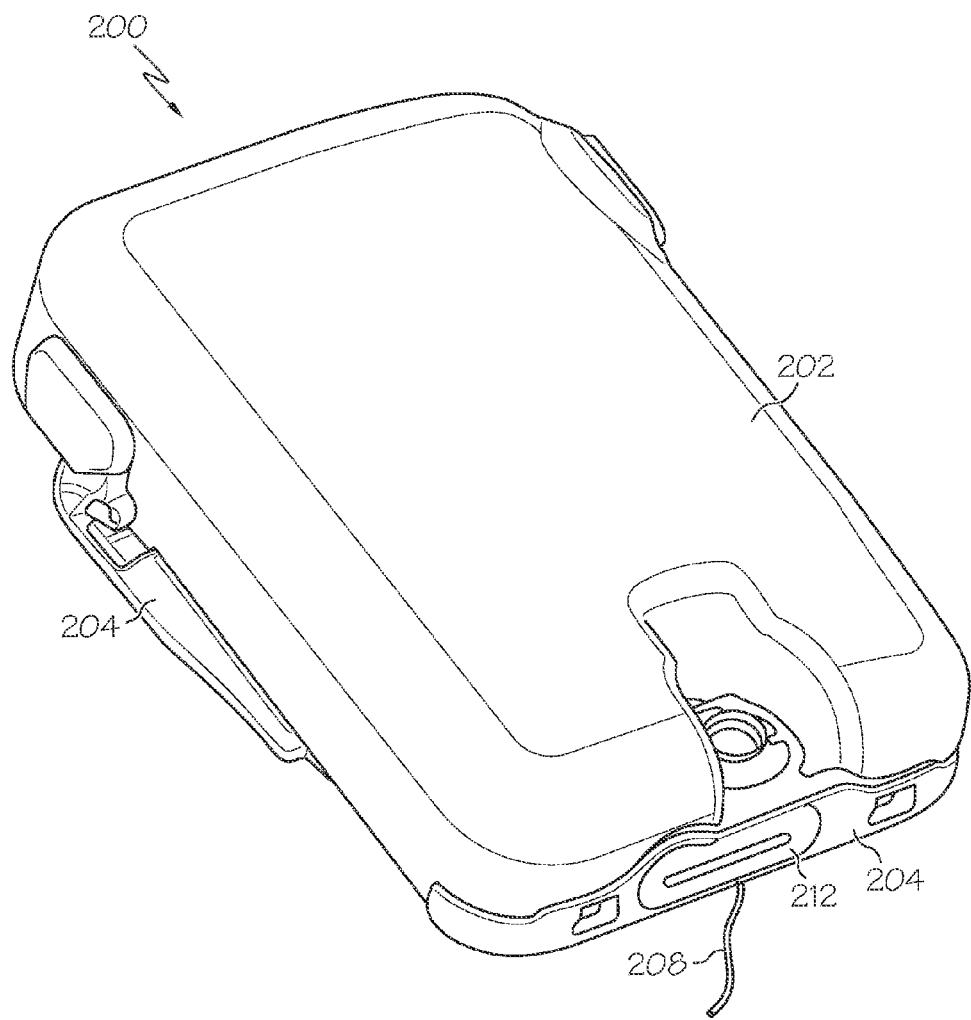
FIG. 2 is a perspective view of an exemplary embodiment of a fluid infusion device suitable for use in the infusion system of FIG. 1.
Figure 3:
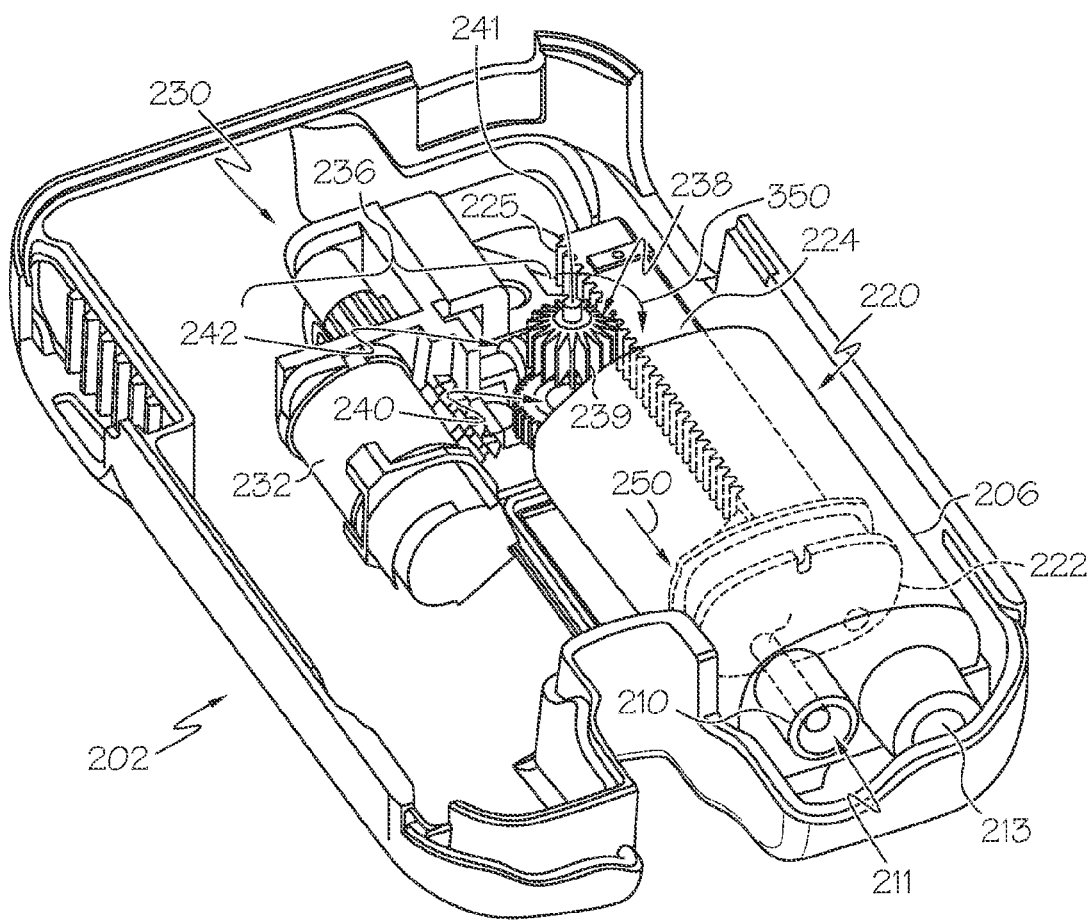
FIG. 3 is a perspective view that depicts internal structure of the durable housing of the fluid infusion device shown in FIG. 2.

FIGS. 2-7 depict an exemplary embodiment of a fluid infusion device 200 suitable for use as the infusion device 102 in the infusion system 100 of FIG. 1. FIGS. 2-3 depict perspective views of the fluid infusion device 200, which includes a durable housing 202 and a base plate 204. While FIG. 2 depicts the durable housing 202 and the base plate 204 as being coupled together, in practice, the durable housing 202 and/or the base plate 204 may include features, structures, or elements to facilitate removable coupling (e.g., pawls, latches, rails, slots, keyways, buttons, or the like) and accommodate a removable/replaceable fluid reservoir 206. As illustrated in FIG. 3, in exemplary embodiments, the fluid reservoir 206 mates with, and is received by, the durable housing 202. In alternate embodiments, the fluid reservoir 206 mates with, and is received by, the base plate 204.

In exemplary embodiments, the base plate 204 is temporarily adhered to the skin of the user, as illustrated in FIG. 1 using, for example, an adhesive layer of material. After the base plate 204 is affixed to the skin of the user, a suitably configured insertion device or apparatus may be used to insert a fluid delivery needle or cannula 208 into the body of the user. The cannula 208 functions as one part of the fluid delivery path associated with the fluid infusion device 200. The durable housing 202 receives the fluid reservoir 206 and retains the fluid reservoir 206 in a substantially fixed position and orientation with respect to the durable housing 202 and the base place 204 while the durable housing 202 and the base plate 204 are coupled. The durable housing 202 is configured to secure to the base plate 204 in a specified orientation to engage the fluid reservoir 206 with a reservoir port receptacle formed in the durable housing 202. In particular embodiments, the fluid infusion device 200 includes certain features to orient, align, and position the durable housing 202 relative to the base plate 204 such that when the two components are coupled together, the fluid reservoir 206 is urged into the reservoir port receptacle to engage a sealing assembly and establish a fluid seal, as described in more detail below.

In exemplary embodiments, the fluid reservoir 206 includes a fluid delivery port 210 that cooperates with the reservoir port receptacle to establish a fluid delivery path. In this regard, the fluid delivery port 210 has an interior 211 defined therein that is shaped, sized, and otherwise configured to receive a sealing element when the fluid reservoir 206 is engaged with the reservoir port receptacle on base plate 204. The sealing element forms part of a sealing assembly for the fluid infusion device 200 and preferably includes one or more sealing elements and/or fluid delivery needles configured to establish fluid communication from the interior of the reservoir 206 to the cannula 208 via the fluid delivery port 210 and a mounting cap 212, and thereby establish a fluid delivery path from the reservoir 206 to the user via the cannula 208. In the illustrated embodiment, the fluid reservoir 206 includes a second fluid port for receiving fluid. For example, the second fluid port 213 may include a pierceable septum, a vented opening, or the like to accommodate filling (or refilling) of the fluid reservoir 206 by the patient, a doctor, a caregiver, or the like.

As illustrated in FIG. 3, the reservoir 206 includes a barrel 220 for containing fluid and a plunger 222 (or stopper) positioned to push fluid from inside the barrel 220 of the reservoir 206 along the fluid path through the cannula 208 to the user. A shaft 224 is mechanically coupled to or otherwise engages the plunger 222, and the shaft 224 has exposed teeth 225 that are configured to mechanically couple or otherwise engage the shaft 224 with a gear 238 of a drive system 230 contained in the durable housing 202. In this regard, the shaft 224 functions as a rack gear as part of a rack and pinion gear configuration, as described in greater detail below. Although the subject matter may be described herein in the context of the shaft 224 being integral with or otherwise part of the plunger 222, in practice, the shaft 224 and the plunger 222 may be provided separately.

FIGS. 4-7 depict perspective and cross-sectional views of the drive system 230 provided in the durable housing 202. Various aspects of the motor drive system 230 may be similar to those described in U.S. patent application Ser. No. 13/049,803. The drive system 230 includes a motor 232 having a rotor 530 that is mechanically coupled to a gear assembly 236 that translates rotation of the rotor 530 to translational displacement the plunger 222 in the direction 250 of the fluid delivery port 210 to deliver fluid from the reservoir 206 to a user. Accordingly, the direction 250 may alternatively be referred to herein as the fluid delivery direction 250.

Figure 4:
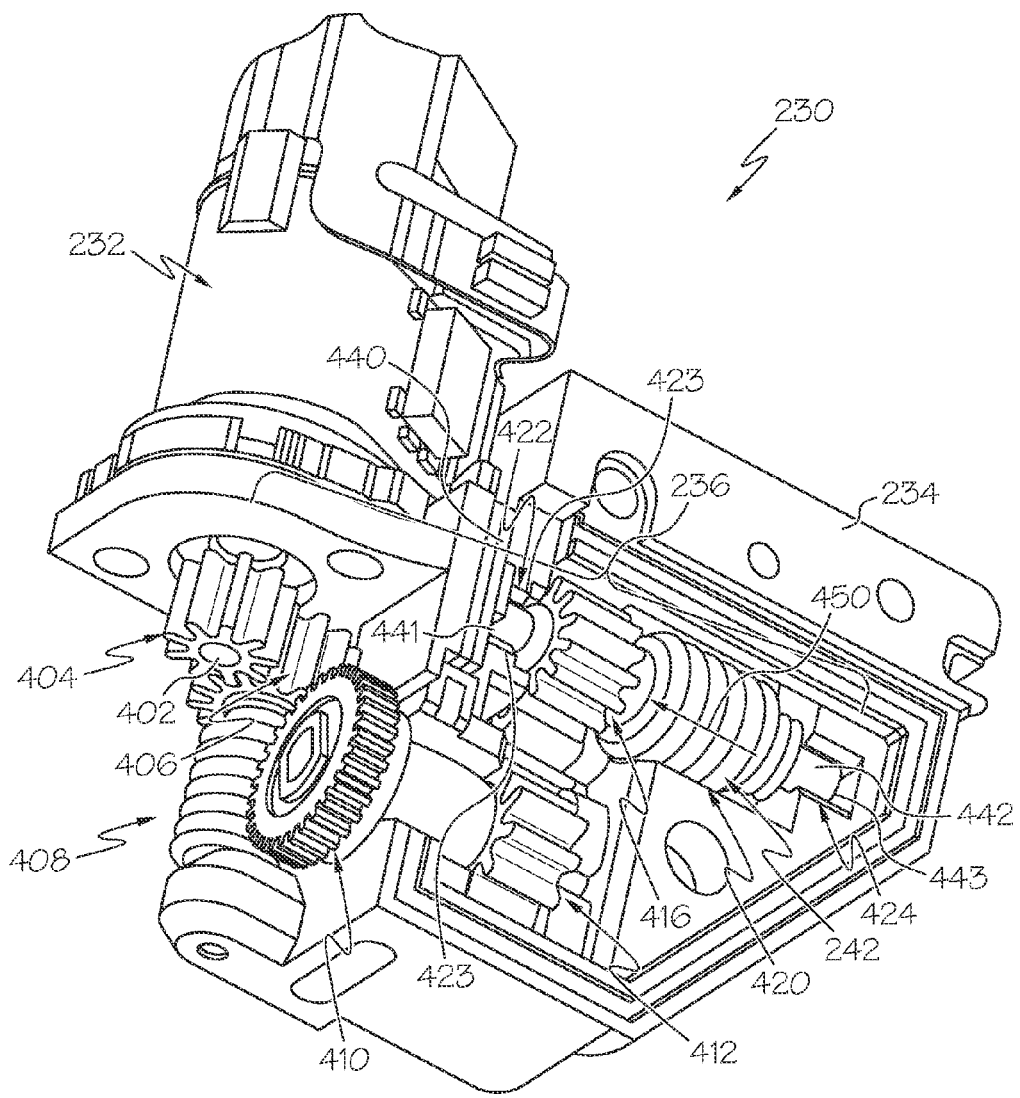
FIG. 4 is a perspective view of the drive system in the durable housing of the fluid infusion device of FIGS. 2-3.
Figure 5:
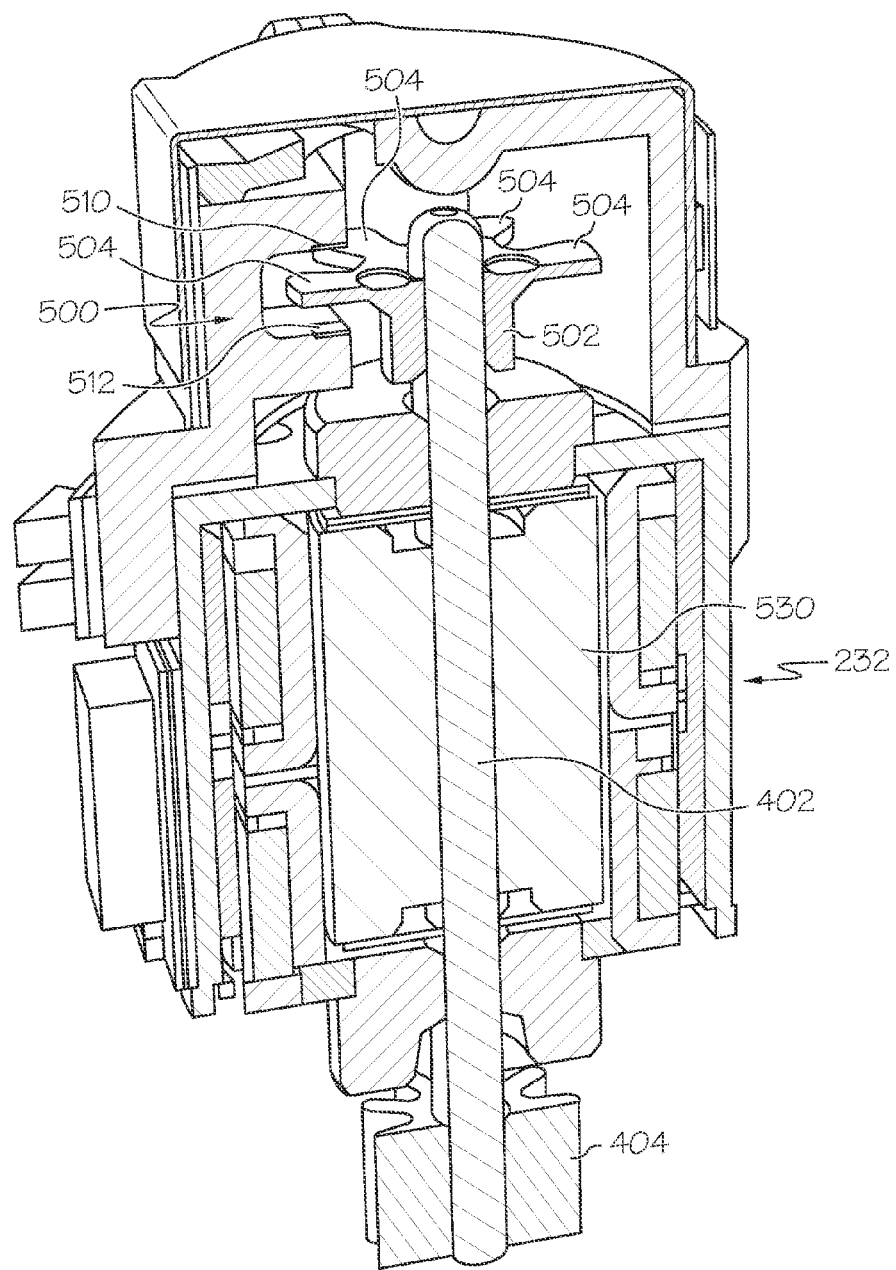
FIG. 5 is cross-sectional perspective view of the motor of drive system of FIG. 4 illustrating a sensor integrated therein.
Figure 6:
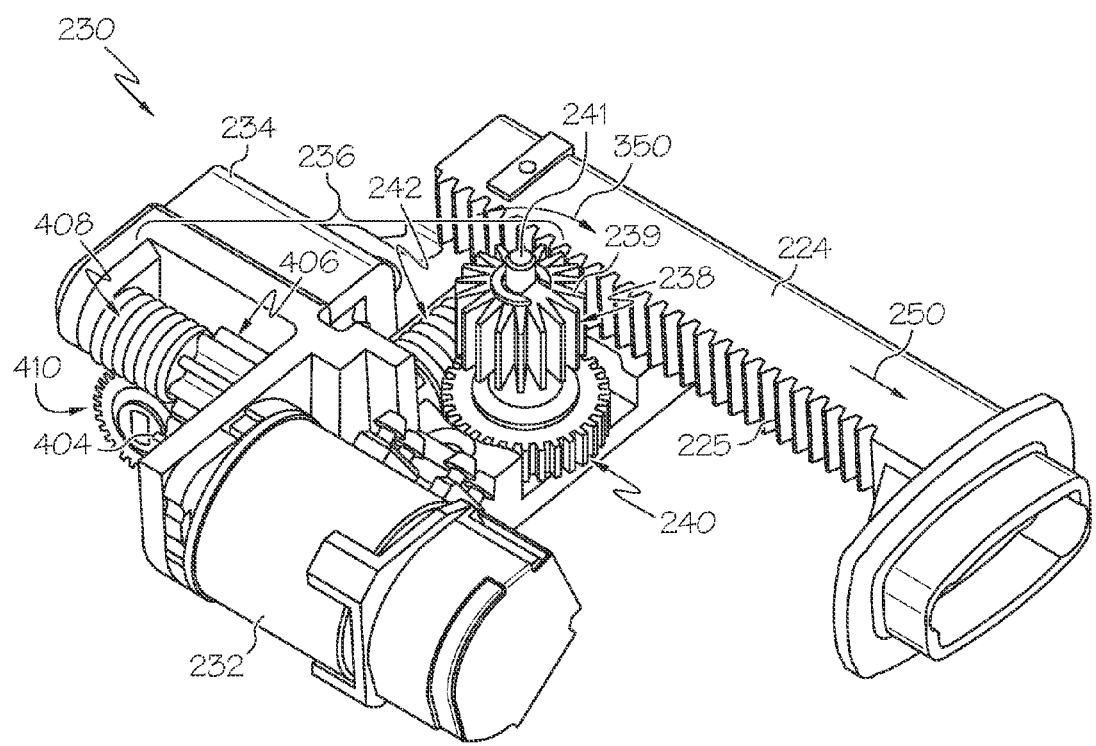
FIG. 6 is a perspective view illustrating the drive system engaged with the shaft of the plunger when the fluid reservoir is seated within the durable housing of FIG. 3.

In exemplary embodiments, the motor 232 is realized as a DC motor, such as a stepper motor or brushless DC motor capable of precisely controlling the amount of displacement of the plunger 222 during operation of the infusion device 200, as described in greater detail below. As best illustrated in FIGS. 4-5, in exemplary embodiments, the rotor 530 of the motor 232 is mechanically coupled to a rotary shaft 402, which, in turn, is mechanically coupled to a first gear 404 of the gear assembly 236. In the illustrated embodiment of FIGS. 4-5, the first gear 404 is coaxial and/or concentric to and disposed about the rotary shaft 402, and the first gear 404 is affixed to or otherwise integrated with the rotary shaft 402 such that the first gear 404 and the rotary shaft 402 rotate in unison. The gear assembly 236 also includes a pinion gear 238 having exposed teeth 239 that are configured to mate with or otherwise engage the exposed teeth 225 on the shaft 224 when the reservoir 206 is seated in the durable housing 202, such that rotation or displacement of the pinion gear 238 in rotational delivery direction 350 produces a corresponding linear displacement of the shaft 224 and/or plunger 222 in the fluid delivery direction 250 to deliver fluid to the user. As described in greater detail below, the gear assembly 236 includes various additional gears and potentially other drive train components configured to mechanically couple the first gear 404 to the pinion gear 238 so that rotation (or displacement) of the first gear 404 produces a corresponding rotation (or displacement) of the pinion gear 238.

During operation of the fluid infusion device 200, when the motor 232 is operated to rotate the rotor 530, the rotary shaft 402 rotates in unison with the rotor 530 to cause a corresponding rotation of the first gear 404, which, in turn, actuates the gears of the gear assembly 236 to produce a corresponding rotation or displacement of the pinion gear 238, which, in turn, displaces the shaft 224. In this manner, the rotary shaft 402 translates rotation (or displacement) of the rotor 530 into a corresponding rotation (or displacement) of the gear assembly 236 such that the teeth 239 of the pinion gear 238 to apply force to the teeth 225 of the shaft 224 of the plunger 222 in the fluid delivery direction 250 to thereby displace the plunger 222 in the fluid delivery direction 250 and dispense, expel, or otherwise deliver fluid from the barrel 220 of the reservoir 206 to the user via the fluid delivery path provided by the cannula 208.

Referring to FIG. 5, in an exemplary embodiment, a sensor 500 is configured to measure, sense, or otherwise detect rotation (or displacement) of the rotary shaft 402 and/or the rotor 530 of the motor 232. For convenience, but without limitation, the sensor 500 may alternatively be referred to herein as a motor position sensor or rotor position sensor. In exemplary embodiments, the rotary shaft 402 includes a detectable feature that is measurable or otherwise detectable by the motor position sensor 500. In the illustrated embodiment, a rotary member (or wheel) 502 is provided on the rotary shaft 402 and includes a plurality of protruding features (or arms) 504 that are measurable or otherwise detectable by the motor position sensor 500. In the illustrated embodiment, the wheel 502 is coaxial and/or concentric to and disposed about the rotary shaft 402, and the wheel 502 is affixed to or otherwise integrated with the rotary shaft 402 such that the wheel 502 and the rotary shaft 402 rotate in unison. In this manner, rotation (or displacement) of the wheel 502 corresponds to the displacement of the rotary shaft 402 and/or the rotor 530 of the motor 232.

In exemplary embodiments, the sensor 500 is realized as an incremental position sensor configured to measure, sense, or otherwise detect incremental rotations of the rotary shaft 402 and/or the rotor 530 of the motor 232. For example, in accordance with one or more embodiments, the sensor 500 is realized as a rotary encoder. In alternative embodiments, the sensor 500 may be realized using any other suitable sensor, such as (but not limited to) a magnetic sensor, optical sensor (or other light detector), tactile sensor, capacitive sensor, inductive sensor, and/or the like. In exemplary embodiments, the incremental position sensor 500 may be configured to count or otherwise sense incremental rotations of the motor 232 via the wheel 502, for example, by counting each time a protruding feature 504 passes by the sensor 500. In this regard, when the number of protruding features 504 equals or otherwise corresponds to the number of discrete motor steps of the stepper motor 232, the incremental position sensor 500 counts or otherwise senses the number of motor steps traversed by the rotary shaft 402 and/or rotor of the motor 232. In some embodiments, the sensor 500 includes an emitter 510 and a detector 512 disposed on opposite sides of the wheel 502 such that at least a portion of the protruding features 504 passes between the emitter 510 and the detector 512 as the wheel 502 rotates. In this regard, the sensor 500 may detect or otherwise count each instance when a protruding feature 504 interrupts a transmission from the emitter 510 to the detector 512. Alternatively, the sensor 500 may detect or otherwise count each instance a transmission from the emitter 510 to the detector 512 is uninterrupted or otherwise completed (e.g., via gaps between protruding features 504).

Referring now to FIGS. 3-7, in exemplary embodiments, the gear assembly 236 includes a spur gear 240 that is mechanically coupled to the pinion gear 238 via a common axle 241 so that the spur gear 240 and the pinion gear 238 rotate in unison. The gear assembly 236 also includes a worm gear 242 that engages with the teeth of the spur gear 240 to translate rotation of the worm gear 242 into a corresponding rotation of the axle 241 of the pinion gear 238. The worm gear 242 and the spur gear 240 cooperatively provide a worm drive arrangement that prevents the pinion gear 238 from being backdriven by external forces applied (e.g., by the shaft 224 or reservoir 206) to the pinion gear 238 in the direction opposite the fluid delivery direction 250. To put it another way, the motor 232 may be operated to rotate the worm gear 242, and thereby rotate the pinion gear 238 in the positive delivery rotational direction 350, but rotation of the worm gear 242 is not capable of being achieved merely by rotating the pinion gear 238 in the negative delivery direction. Rather, as described in greater detail below, external rotation of the pinion gear 238 results in axial forces applied to the worm gear 242 by the spur gear 240, which, in turn, may result in axial displacement of the worm gear 242.

As best illustrated in FIG. 4, the gear assembly 236 includes a plurality of gears 404, 406, 408, 410, 412, 414, 416 configured to translate rotation of the rotary shaft 402 into a corresponding rotation of the worm gear 242, and thereby, a corresponding rotation of the pinion gear 238. As illustrated, the gear assembly 236 includes a spur gear 406 having teeth that engage with the gear 404 coupled to the rotary shaft 402, so that rotation of the gear 404 results in a corresponding amount of rotation of the spur gear 406. The spur gear 406 shares a common axle with a worm gear 408 so that the spur gear 406 and the worm gear 408 rotate in unison, with the worm gear 408 engaging another spur gear 410 to provide another worm drive arrangement. Spur gear 410 shares a common axle with another spur gear 412 so that the gears 410, 412 rotate in unison. Spur gear 412 engages another spur gear 414 (illustrated in FIG. 7), which, in turn, engages a spur gear 416 sharing a common axle 442 with the worm gear 242, so that the spur gear 416 and the worm gear 242 rotate in unison. By virtue of this configuration, the worm gear 408 translates rotation of the spur gear 404 into a corresponding rotation of the spur gear 412, which engages the spur gear 414 to rotate the spur gear 416 and the axle 442, and thereby rotate the worm gear 242. Thus, the rotary shaft 402 is coupled to the worm gear 242, and thereby, the pinion gear 238, so that rotation of the rotary shaft 402 produces a corresponding rotation of the worm gear 242, which, in turn, produces a corresponding rotation of the pinion gear 238.

Still referring to FIGS. 3-7, in exemplary embodiments, the durable housing 202 includes or otherwise incorporates a frame structure 234 that provides support to various gears of the gear assembly 236. In this regard, the frame structure 234 is realized as a substantially rigid material that the axles of the gears may be mounted to, restrained by, or otherwise supported by to ensure that the gear assembly 236 translates rotation of the rotary shaft 402 into rotation of the pinion gear 238 without gears of the gear assembly 236 becoming disengaged. Additionally, the frame structure 234 may be utilized to mount the motor 232 to the gear assembly 236 so that the rotary shaft 402 is maintained in engagement with the spur gear 404.

Figure 7:
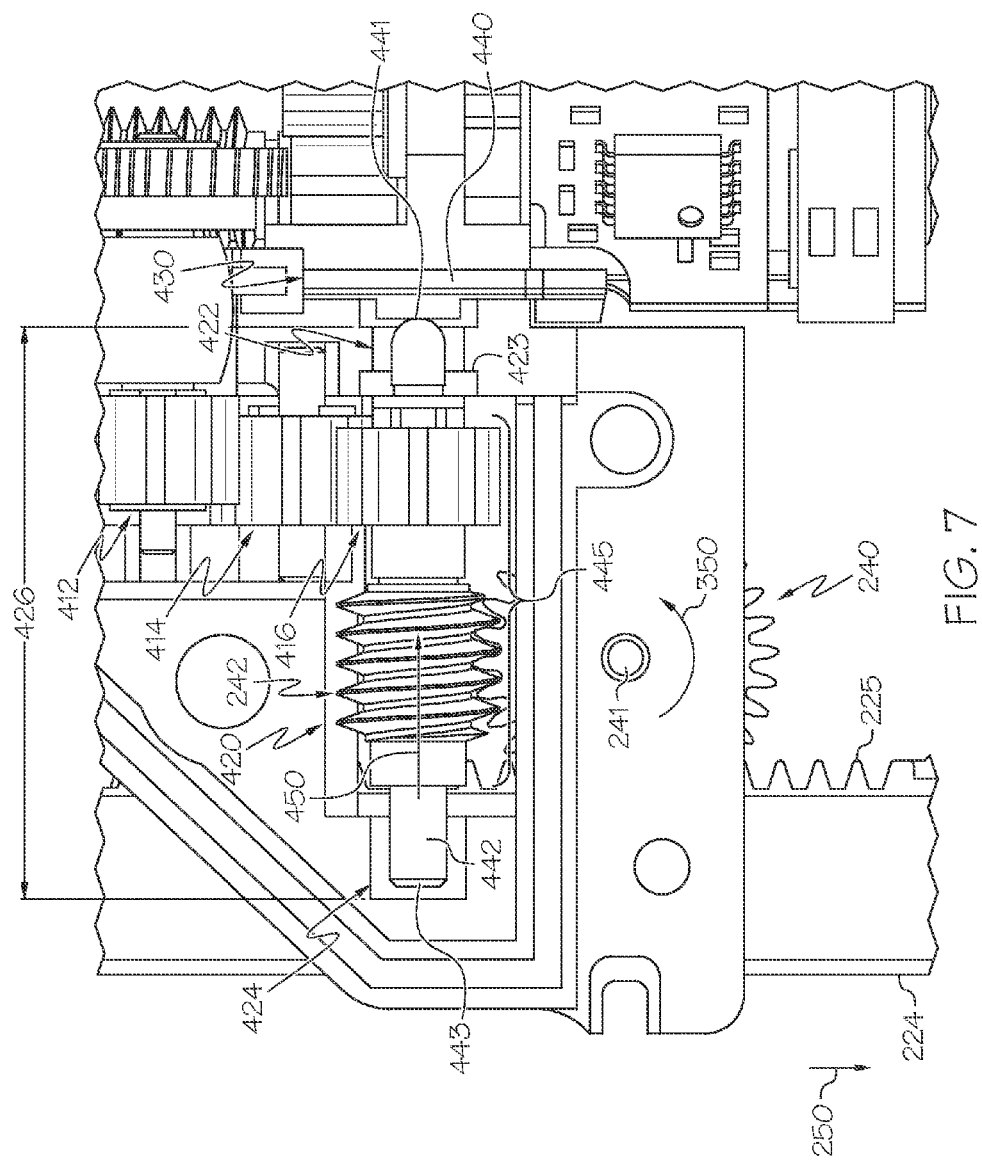
FIG. 7 is a plan view illustrating the gear assembly of the drive system engaged with the shaft of the plunger when the fluid reservoir is seated within the durable housing of FIG. 3.

As best illustrated by FIG. 4 or FIG. 7, the frame structure 234 includes a voided region 420 that substantially circumscribes the axle 442 of the worm gear 242 about its longitudinal axis to maintain the axle 442 and/or the worm gear 242 in a substantially fixed plane with respect to the frame structure 234. In this regard, the illustrated voided region 420 includes an opening 422 at one end having a first end 441 of the axle 442 disposed therein to prevent displacement of that end 441 of the axle 442 perpendicularly to its longitudinal axis, and similarly, the voided region 420 includes a cutout portion 424 of the frame structure 234 that has the opposite end 443 of the axle 442 disposed therein to prevent displacement of that end 443 of the axle 442 perpendicularly to its longitudinal axis. In this manner, the frame structure 234 restricts or otherwise prevents displacement of the axle 442 and/or worm gear 242 perpendicularly to its longitudinal axis. As described in greater detail below, the total length (illustrated by arrow 426) of the voided region 420 is greater than the length of the axle 442 so that the axle 442 (and thereby, the worm gear 242) is capable of axial displacement until either end 441, 443 of the axle 442 is restrained or otherwise prevented from further axial displacement by the frame structure 234. In this regard, the respective circumferences of the opening 422 and the cutout portion 424 are less than the circumference of the central portion 445 of the axle 442 to limit axial displacement of the worm gear 242 so that the spur gear 416 is maintained in engagement with the spur gear 414 as the axle 442 is displaced.

In addition to the voided region 420, the frame structure 234 also includes another cutout region (or slot) 430 aligned with the longitudinal axis of the axle 442 and the opening 422 at the end of the voided region 420 to measure an axial force exerted on or otherwise provided by the axle 442 in an axial direction 450. In this regard, when the motor 232 is operated to rotate the pinion gear 238 in the direction 350 that results in displacement of the shaft 224 in the fluid delivery direction 250, the corresponding rotation of the worm gear 242 results in the axle 442 of the worm gear 242 being displaced in the axial direction 450 towards the force sensor 440 (e.g., by virtue of the resistance force applied or otherwise transferred by the spur gear 240) so that the end 441 of the axle 442 of the worm gear 242 extends through the opening 422 and contacts the force sensor 440, as illustrated in FIG. 7. Thus, the axial direction 450 corresponds to the direction of force applied to the worm gear 242 when the shaft 224 is displaced in the fluid delivery direction 250, and accordingly, may alternatively be referred to herein as the axial delivery direction 450. As external forces resist or otherwise prevent displacement of the shaft 224 and/or plunger 222 in the fluid delivery direction 250 (e.g., due to a fluid path occlusion), rotation of the pinion gear 238 and the spur gear 240 is resisted or otherwise prevented, so that the torque applied by the motor 232 to the worm gear 242 via the gear assembly 236 is translated into an axial force exerted on the force sensor 440 by the axle 442.

Because the worm drive arrangement provided by the worm gear 242 and spur gear 240 is incapable of being backdriven, once the axle 442 of the worm gear 242 is displaced in the axial direction 450 and restricted from further displacement in the axial direction 450 by the frame structure 234 and/or force sensor 440, the pinion gear 238 is effectively incapable of being rotated by a non-negligible amount in the direction opposite the rotational direction 350 corresponding to the fluid delivery direction 250. In other words, when the gear assembly 236 is in the state depicted in FIG. 7, displacement of the axle 442 of the worm gear 242 is in the axial direction 450 is inhibited, and the pinion gear 238 effectively lacks rotational freedom in the negative delivery rotational direction and is effectively capable of only being rotated unidirectionally in the fluid delivery rotational direction 350. Thus, if the reservoir 206 were inserted into the durable housing 202 and into engagement with the pinion gear 238 with the gear assembly 236 in the state depicted in FIG. 7, any misalignment of the teeth 225 of the shaft 224 and the teeth 239 of the pinion gear 238 may result in unintended displacement of the shaft 224 in the delivery direction 250 (e.g., by virtue of the worm drive arrangement preventing rotation of the pinion gear 238 in the rotational direction opposite the rotational direction 350 corresponding to the fluid delivery direction 250). Accordingly, in exemplary embodiments, in the absence of the reservoir 206 and/or shaft 224, the axle 442 of the worm gear 242 is biased or otherwise displaced axially in the direction opposite the axial delivery direction 450 and away from the force sensor 440 and/or the lip portion 423 of the frame structure 234 that restrict displacement in the axial direction 450, thereby increasing the distance between the force sensor 440 and/or the lip portion 423 of the frame structure 234 that restrict displacement in the axial direction 450 so that the pinion gear 238 is capable of being rotated in the direction opposite the fluid delivery rotational direction.

Figure 8:
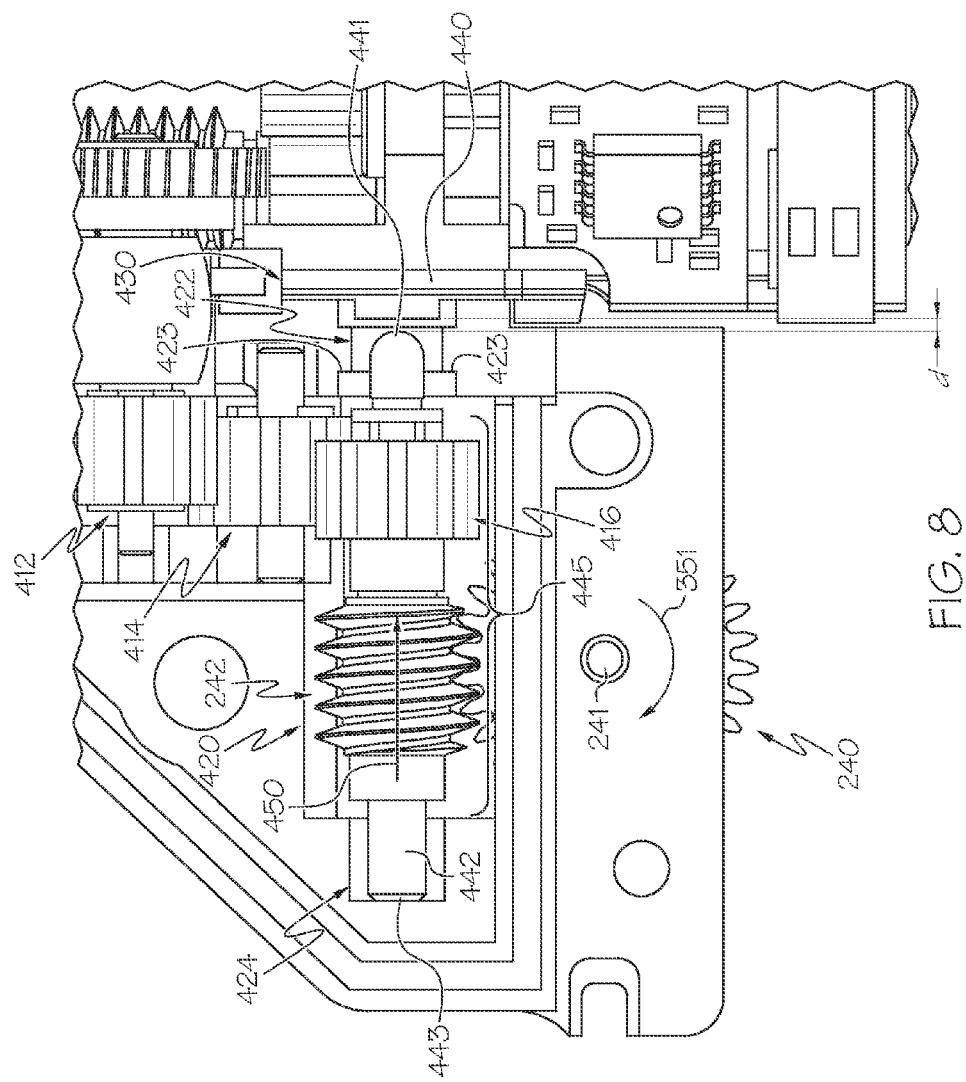
FIG. 8 is a plan view illustrating gear assembly in a reset state with the fluid reservoir removed from the durable housing of FIG. 3 in accordance with one embodiment.

Turning now to FIG. 8, when the reservoir 206 is removed from the durable housing 202, the gear assembly 236 may be configured in a reset state that provides, to the pinion gear 238, rotational freedom in the negative delivery rotational direction 351. In the gear assembly reset state, the end 441 of the axle 442 of the worm gear 242 is biased or otherwise displaced axially away from the force sensor 440 (e.g., by a distance d), or alternatively, away from the lip portion 423 or any other restraining feature of the frame structure 234, in order to provide freedom for the axle 442 and/or worm gear 242 to be displaced in the axial delivery direction 450. In this regard, when the reservoir 206 is subsequently inserted in the durable housing 202, any forces applied to the pinion gear 238 in the negative delivery rotational direction 351 by the shaft 224 (e.g., due to misalignment of teeth 225 with respect to teeth 239) are transferred by the spur gear 240 to displace the worm gear 242 in the axial direction 450 (e.g., via the spur gear 240 rotating in unison with the pinion gear 238 in the negative delivery rotational direction 351 about axle 241) without displacing the shaft 224 in the delivery direction 250, thereby preventing inadvertent delivery of fluid from the reservoir 206.

As described in greater detail below in the context of FIGS. 9-10, in accordance with one or more embodiments, the motor 232 is rewound or otherwise operated to rotate the worm gear 242 in the direction that results in the axle 442 being displaced in the direction opposite the axial delivery direction 450 (e.g., by operating the motor 232 is operated to rotate the pinion gear 238 in the direction that would result in displacement of the shaft 224 in the direction opposite the fluid delivery direction 250) until the end 443 of the axle 442 residing within the cutout portion 424 contacts the frame structure 234, thereby preventing further axial displacement of the axle 442 away from the force sensor 440. In this situation, the pinion gear 238 has rotational freedom in the negative delivery rotational direction, so that if the reservoir 206 were inserted into the durable housing 202 and into engagement with the pinion gear 238 in this situation, the pinion gear 238 rotates in the negative delivery rotational direction 351 to accommodate any misalignment of the teeth 225 of the shaft 224 and the teeth 239 of the pinion gear 238, thereby preventing displacement of the shaft 224 in the fluid delivery direction 250. In this regard, by biasing or otherwise displacing the worm gear 242 and/or axle 442 away from the force sensor 440 and/or the lip portion 423 the frame structure 234 that restrict displacement in the axial direction 450, the rotation of the pinion gear 238 in the negative delivery rotational direction 351 is translated to axial displacement of the worm gear 242 and/or axle 442 in the axial delivery direction 450.

As described in greater detail below in the context of FIGS. 12-13, in accordance with one or more alternative embodiments, a mechanical element is provided within the voided region 420 between the lip portion 423 of the frame structure 234 and the central portion 445 of the axle 442 to apply a force to the axle 442 of the worm gear 242 in the direction opposite the axial delivery direction 450. Thus, in the absence of a reservoir 206 and/or shaft 224 engaged with the pinion gear 238, the mechanical element displaces the axle 442 and/or worm gear 242 away from the force sensor 440 and/or the lip portion 423 of the frame structure 234 that would restrict displacement of the axle 442 and/or worm gear 242 in the axial direction 450 so that the pinion gear 238 is capable of being rotated in the negative delivery rotational direction 351.

Figure 9:
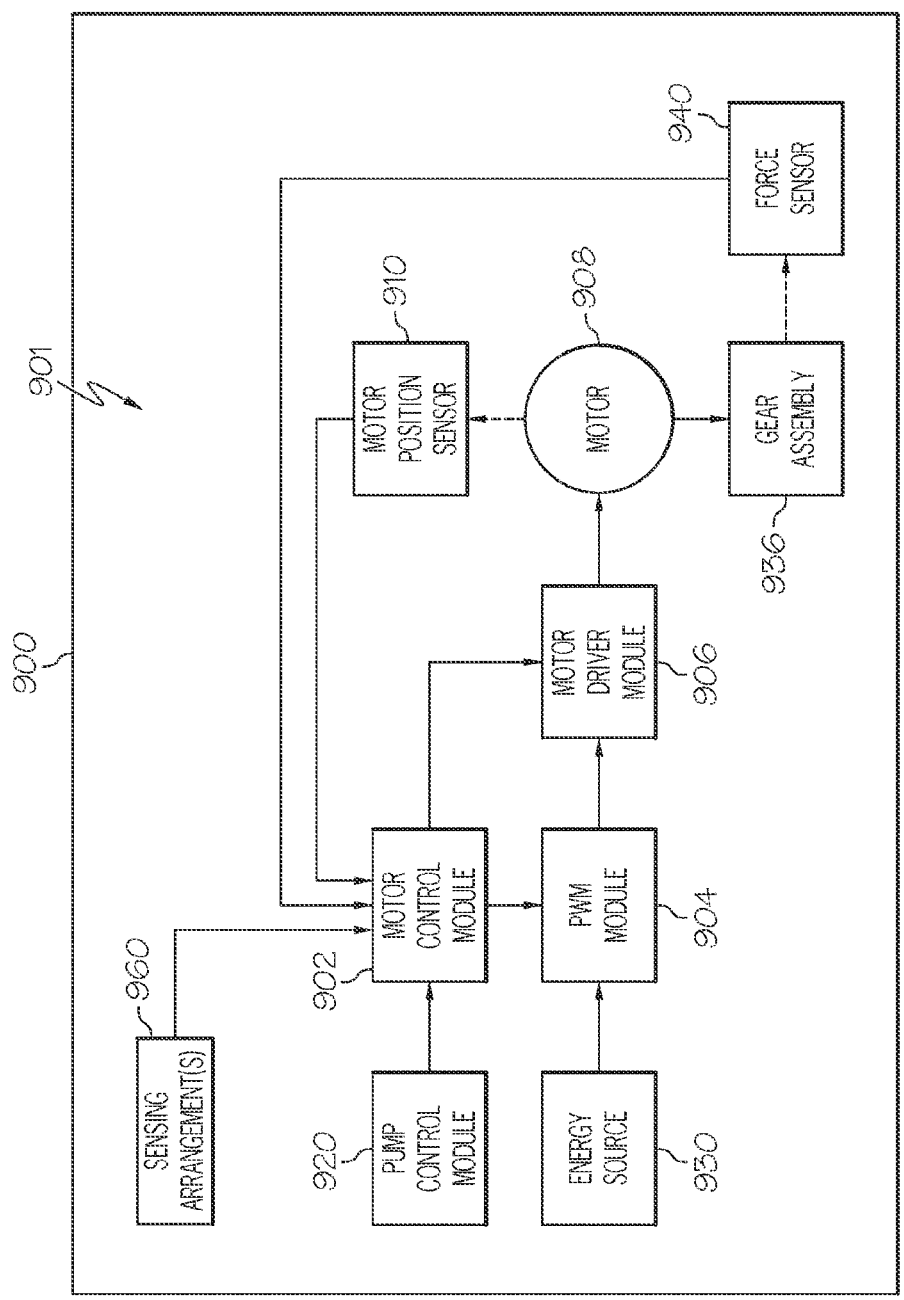
FIG. 9 is a block diagram of an exemplary control system suitable for use in a fluid infusion device, such as the fluid infusion device of FIG. 2.

FIG. 9 depicts an exemplary embodiment of a control system 901 suitable for use with an infusion device 900 in an infusion system, such as infusion device 200 or infusion device 102 in the infusion system 100. The illustrated control system 901 includes, without limitation, a motor control module 902, a pulse-width modulation (PWM) module 904, a motor driver module 906, a motor 908 (e.g., motor 232), and a motor (or rotor) position sensor 910 (e.g., sensor 500). The control system 901 is suitably configured to operate the motor 908 to displace a plunger (e.g., plunger 222) of a reservoir (e.g., reservoir 206) and provide a desired amount of fluid to a user in response to a dosage command indicative of the desired amount of fluid to be delivered that is received from a pump control system 920. In this regard, the pump control system 920 generally represents the electronics and other components of the infusion system that process sensor data (e.g., from sensing arrangement 104) pertaining to a condition of the user and control operation of the fluid infusion device 900 according to a desired infusion delivery program in a manner that is influenced by sensor data measured by and/or received from the sensing arrangement 104 or otherwise dictated by the user. In practice, the features and/or functionality of the pump control system 920 may be implemented by control electronics located in the fluid infusion device 102, 200, the CCD 106 and/or the computer 108. It should be understood that FIG. 9 is a simplified representation of the control system 901 for purposes of explanation and is not intended to limit the subject matter described herein in any way. For example, in practice, the features and/or functionality of the motor control module 902 may implemented by or otherwise integrated into the pump control system 920, or vice versa.

In the illustrated embodiment, the PWM module 904 generally represents the combination of circuitry, hardware and/or other electrical components configured to generate a pulse-width modulated voltage output applied to the motor 908 via the motor driver module 906. In an exemplary embodiment, the PWM module 904 is coupled to an energy source 930, such as a battery housed within the infusion device 200 (e.g., in the durable housing 202), to receive a supply voltage. Based on a duty cycle setting for the PWM module 904, the PWM module 904 generates or otherwise produces a pulse-width modulated voltage output that oscillates between the supply voltage provided by the energy source 930 and a ground (or reference) voltage over a time interval (e.g., the PWM period), wherein the pulse-width modulated voltage output is equal to the supply voltage for a percentage of the time interval corresponding to the duty cycle setting. For example, if the supply voltage provided by the energy source 930 is equal to five volts and the duty cycle setting is equal to 30%, then the pulse-width modulated voltage output generated by the PWM module 904 may be a square wave having a magnitude equal to five volts for 30% of the time interval and zero volts for the remaining 70% of the time interval. In this regard, the duty cycle setting corresponds to the width of a portion of the square wave (e.g., the portion corresponding the supply voltage), and accordingly, the duty cycle setting may alternatively be referred to herein as the PWM width setting. In exemplary embodiments, the control module 902 is coupled to the PWM module 904 to adjust, modify, or otherwise control the duty cycle setting of the PWM module 904, as described in greater detail below.

In an exemplary embodiment, the motor 908 is a stepper motor or brushless DC motor having a toothed rotor and a number of sets of windings, wherein the number of teeth on the rotor along with the number of winding sets and the physical arrangement of the winding sets with respect to the rotor teeth provides a finite number of motor steps within a revolution of the rotor. In this regard, as used herein, a "motor step" or any variant thereof should be understood as referring to an incremental rotation of the rotor of the motor 908 that is dictated by the number of teeth of the rotor along with the number and/or arrangement of the winding sets. As described above in the context of FIGS. 2-8, in an exemplary infusion pump embodiment, the rotor of the motor 908 is mechanically coupled to the plunger of the reservoir via a gear assembly 936 (e.g., gear assembly 236) and a shaft (e.g., shaft 224), wherein the gear assembly 936 translates rotation of the rotor of the motor 908 into a corresponding amount of displacement of the shaft, which in turn, displaces the plunger (e.g., plunger 222) into the barrel (e.g., barrel 220) of the reservoir (e.g., reservoir 206) to deliver fluid (e.g., insulin) to the body of a user.

Still referring to FIG. 9, the motor driver module 906 generally represents the combination of circuitry, hardware and/or other electrical components configured to sequentially apply a voltage provided at a supply voltage input of the motor driver module 906 to one or more sets of windings of the motor 908 in a particular order to produce a corresponding number of commanded motor steps of rotation by the motor 908. In the illustrated embodiment, the supply voltage input of the motor driver module 906 is coupled to the output of the PWM module 904, such that the motor driver module 906 provides the pulse-width modulated voltage from the PWM module 904 to the one or more sets of windings of the motor 908 in a particular order under control of the control module 902. In this regard, in some embodiments, the motor driver module 906 is coupled to the control module 902 to receive a commanded number of motor steps from the control module 902, wherein in response to the commanded number of motor steps, the motor driver module 906 sequentially applies the pulse-width modulated voltage from the PWM module 904 to the sets of windings of the motor 908 in the appropriate order to produce the commanded number of motor steps. In other embodiments, the control module 902 may operate the switches and/or other circuitry of the motor driver module 906 to produce the commanded number of motor steps. The frequency at which the motor driver module 906 is operated (e.g., the frequency at which the pulse-width modulated voltage is changed from being applied to one winding set to another winding set) is less than the frequency of the pulse-width modulated voltage output from the PWM module 904, such that the pulse-width modulated voltage output oscillates between the supply voltage and the ground voltage multiple times over the time period (e.g., the inverse of the motor driver frequency) during which the pulse-width modulated voltage output is applied to a particular set of windings of the motor 908.

In an exemplary embodiment, the motor position sensor 910 is realized as an incremental position sensor, such as a rotary encoder, that is configured to sense, measure, or otherwise detect an incremental rotation of the rotor of the motor 908, in a similar manner as described above in the context of the sensor 500 of FIG. 5. In exemplary embodiments, the resolution of the position sensor 910 is greater than or equal to the resolution of the motor 908, that is, the number of discrete incremental rotations measurable by the position sensor 910 over one revolution of the rotor of the motor 908 (e.g., the number of detectable features 504) is greater than or equal to the number of discrete motor steps over one revolution of the rotor of the motor 908. In accordance with one or more embodiments, the output of the position sensor 910 is coupled to the control module 902 to provide dynamic closed-loop PWM control of the motor 908, for example, as described in U.S. patent application Ser. No. 13/425,174, which is assigned to the assignee of the present application and incorporated by reference herein.

Still referring to FIG. 9, the control module 902 generally represents the hardware, software, firmware and/or combination thereof that is configured to receive or otherwise obtain a commanded dosage from the pump control system 920, convert the commanded dosage to a commanded number of motor steps, and command, signal, or otherwise operate the motor driver module 906 to cause the motor 908 to produce the commanded number of motor steps. Depending on the embodiment, the control module 902 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the control module 902, or in any practical combination thereof. In exemplary embodiments, the control module 902 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the control module 902. The computer-executable programming instructions, when read and executed by the control module 902, cause the control module 902 to perform the tasks, operations, functions, and processes described in greater detail below.

Additionally, as described in greater detail below in the context of FIG. 10, in accordance with one or more embodiments, the control module 902 detects or otherwise identifies a reset condition, and in response, commands, signals, or otherwise operates the motor 908 to reset the gear assembly 936 to a reset state in which the gear of the gear assembly 936 that engages the shaft of the reservoir (e.g., the pinion gear 238) has rotational freedom in a direction opposite the rotational direction corresponding to the fluid delivery direction, as illustrated in FIG. 8. For example, a fluid infusion device may include a sensing arrangement 960 that includes a sensing element configured to measure, sense, or otherwise detect the presence of the reservoir, wherein the control module 902 is coupled to the sensing arrangement 960 and detects or otherwise identifies a reset condition in response to the sensing element failing to detect the presence of the reservoir. In one or more embodiments, the shaft (e.g., shaft 224) of the reservoir includes one or more detectable features that are sensed or otherwise detected by the sensing arrangement 960 when the reservoir is seated in the fluid infusion device 900.

Figure 10:
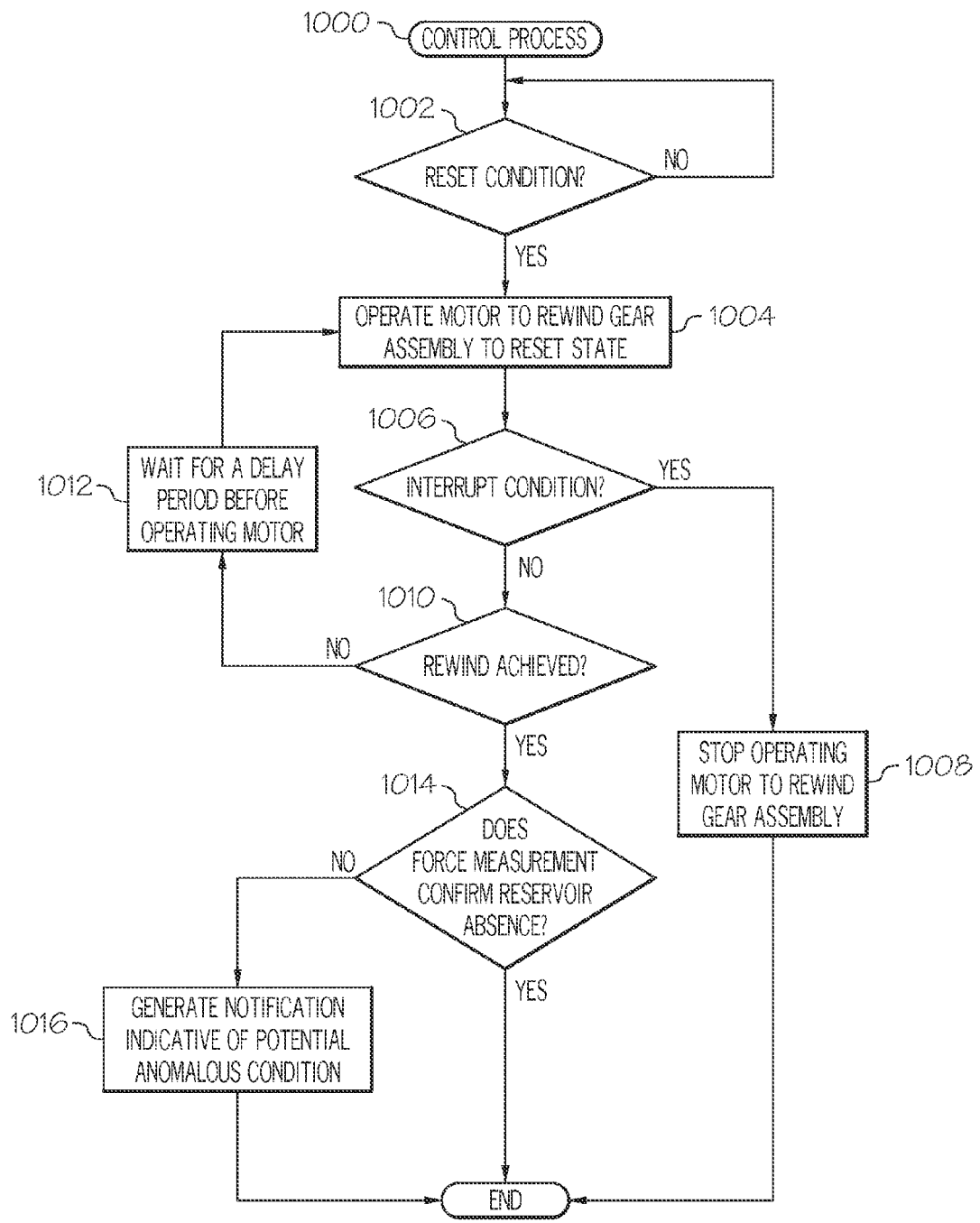
FIG. 10 is a flow diagram of an exemplary control process suitable for use with the control system of FIG. 9 to provide rotational freedom to a gear that engages a shaft of a fluid reservoir.

FIG. 10 depicts an exemplary control process 1000 suitable for implementation by a control system in a fluid infusion device operate an infusion device to deliver fluid to a user while accommodating removal and/or insertion of the fluid reservoir from/to the infusion device. The various tasks performed in connection with the control process 1000 may be performed by software, hardware, firmware, or any combination thereof. For illustrative purposes, the following description refers to elements mentioned above in connection with FIGS. 1-9. In practice, portions of the control process 1000 may be performed by different elements of the control system 901, such as, for example, the control module 902, the PWM module 904, the motor driver module 906, the motor 908, the position sensor 910, and/or the sensing arrangement 960. It should be appreciated that the control process 1000 may include any number of additional or alternative tasks, the tasks need not be performed in the illustrated order and/or the tasks may be performed concurrently, and/or the control process 1000 may be incorporated into a more comprehensive procedure or process having additional functionality not described in detail herein. Moreover, one or more of the tasks shown and described in the context of FIG. 10 could be omitted from a practical embodiment of the control process 1000 as long as the intended overall functionality remains intact.

In exemplary embodiments, the control process 1000 begins by detecting or otherwise identifying a reset condition (task 1002). As used herein, a reset condition should be understood as referring to an operational condition or state of a fluid infusion device in which it is desirable to accommodate subsequent insertion of a fluid reservoir in the fluid infusion device. For example, the control module 902 may identify a reset condition when the sensing arrangement 960 fails to detect or otherwise sense the presence of the reservoir within a corresponding voided region of the durable housing 202. In another embodiment, the control module 902 may identify a reset condition in response to receiving an input from a user (e.g., via CCD 106) that is indicative of a desire to reset the gear assembly. In accordance with one or more exemplary embodiments, the control process 1000 identifies a reset condition by performing the reset condition identification process 1100 described in greater detail below in the context of FIG. 11.

In the absence of a reset condition, the control module 902 may maintain normal operation of the motor 232, 908 in the fluid infusion device 102, 200. For example, the control module 902 may obtain commands from the pump control system 920 corresponding to the desired dosage and operate the motor 908 to rotate the rotor by an amount that produces an amount of displacement of the shaft 224 and/or plunger 222 of the reservoir 206, 950 that corresponds to the desired dosage. For example, the pump control system 920 may determine or otherwise receive (e.g., from the CCD 106 and/or the computer 108) a dose (or bolus) of fluid to be provided to the user based on a sensed condition of the user (e.g., a blood glucose level). In some embodiments, the pump control system 920 converts the amount of fluid to be provided to the user into a commanded displacement of the plunger, converts the commanded displacement of the plunger to a corresponding number of motor steps (or incremental rotations) based on the relationship between one motor step of rotation and the resulting linear displacement of the shaft 224 and/or plunger 222, and provides that commanded number of motor steps to the control module 902. In other embodiments, the pump control system 920 provides the amount of fluid to be provided to the user to the control module 902, wherein the control module 902 converts the commanded dosage into a corresponding number of commanded motor steps based on the amount of displacement of the plunger 222 corresponding to that amount of fluid. Thereafter, in exemplary embodiments, the control module 902 utilizes closed-loop dynamic PWM control by dynamically adjusting the duty cycle setting of the PWM module 904 to ensure the rotor 530 rotates by the commanded amount. For example, the control module 902 may determine an expected number of incremental rotations of the rotor 530 of the motor 232, 908 that should be measured by the position sensor 500, 910 based on the commanded number of motor steps corresponding to the commanded dosage. After operating the motor driver module 906 to produce the commanded number of motor steps of rotation, the control module 902 obtains a measured number of incremental rotations of the rotor of the motor 232, 908 from the position sensor 500, 910, and based on differences between the measured number and the expected number of incremental rotations, increases or otherwise adjusts the PWM width setting of the PWM module 904 to achieve the commanded number of motor steps during subsequent operation of the motor 908.

Still referring to FIG. 10, in response to identifying a reset condition, the control process 1000 continues by signaling, commanding, or otherwise operating the motor to rewind the gear assembly to a reset state and thereby provide, for the gear of the gear assembly that engages or otherwise drives the shaft for the plunger of the reservoir, rotational freedom in the direction opposite the rotational direction corresponding to the fluid delivery direction (task 1004). In this regard, the control module 902 provides commands or signals to the PWM module 904 and/or motor driver module 906 that are intended to cause the rotor 530 of the motor 232, 908 to rotate a desired number of motor steps in the direction that results in the worm gear 242 being axially displaced in the direction opposite the axial delivery direction 450 and away from the force sensor 440 and/or the lip portion 423 of the frame structure 234 that restrain displacement of the worm gear 242 and/or axle 442 in the delivery direction 450. To put it another way, the control module 902 provides commands or signals that would result in retraction of the shaft 224 and/or plunger 222 in the negative fluid delivery direction 250 (if the reservoir 206 were present), effectively rewinding the gear assembly 236 to a reset state where the pinion gear 238 exhibits rotational freedom in the direction opposite the fluid delivery rotational direction 350 (i.e., negative delivery rotational direction 351) by providing a space between the end 441 of the axle 442 and the force sensor 440 and/or the lip portion 423 of the frame structure 234 that allows the worm gear 242 and/or axle 442 to displaced in the axial direction 450 since the worm gear 242 cannot be backdriven by the spur gear 240. In exemplary embodiments, the control module 902 signals, commands, or otherwise operates the motor driver module 906 to achieve a fixed number of motor steps in the negative delivery direction, wherein the fixed number is chosen to overcome static friction in the gear assembly 236, 936 and axially displace the worm gear 242 and/or axle 442 in the negative axial delivery direction until the axial displacement of the worm gear 242 and/or axle 442 is restrained by the frame structure 234 (e.g., by end 443 contacting the frame structure 234). Thus, after the gear assembly 236, 936 is rewound, the end 443 of the axle 442 that is opposite the force sensor 440 contacts or otherwise abuts with the frame structure 234 to prevent displacement of the axle 442 in the direction opposite the axial delivery direction 450. In accordance with one exemplary embodiment, the control module 902 signals or otherwise commands the PWM module 904 to provide PWM signals having a 70% duty cycle or less and a frequency of 1000 pulses per second while signaling, commanding, or otherwise operating the motor driver module 906 to achieve 1800 motor steps in the negative delivery direction.

In exemplary embodiments, while the control process 1000 is operating the motor to rewind the gear assembly, the control process 1000 continually monitors one or for an interrupt condition that indicates that the rewind of the gear assembly should be terminated and stops operating the motor to rewind the gear assembly in response to identifying an interrupt condition (tasks 1006, 1008). For example, a user may reinsert the reservoir 206, 950 (or a new reservoir) or the reservoir 206, 950 may have only been temporarily dislodged within the durable housing 202, in which case, unintended retraction of the plunger 222 would be undesirable. Accordingly, in exemplary embodiments, the control module 902 monitors the sensing arrangement 960 while operating the motor 908 to rewind the gear assembly 236, 936, and in response to the sensing arrangement 960 detecting or otherwise identifying the presence of the reservoir 206, 950 during the gear assembly rewind, the control module 902 identifies an interrupt condition and ceases operating the PWM module 904 and/or motor driver module 906 to rewind the gear assembly 236, 936. When the control process 1000 fails to detect or otherwise identify an interrupt condition, the control process 1000 completes the operating the motor to produce the commanded number of motor steps chosen to rewind the gear assembly.

Still referring to FIG. 10, the control process 1000 continues by determining or otherwise identifying whether the rewind of the gear assembly was achieved by comparing the measured amount of rotation for the rotor of the motor to the commanded amount of rotation (task 1010). In this regard, the motor control module 902 obtains, from the motor position sensor 500, 910, a number of incremental rotations of the rotor 530 of the motor 232, 908 in the negative delivery direction that were detected, sensed, or otherwise measured by the motor position sensor 500, 910. The motor control module 902 converts the commanded number of motor steps in the negative delivery direction to a commanded number of incremental rotations and compares the commanded number of incremental rotations to the measured number of incremental rotations to determine or otherwise identify whether the measured amount of motor rotation in the negative delivery direction is within a threshold value if the commanded amount of motor rotation. In this regard, the threshold value is chosen to be a difference between the measured number of incremental rotations and the commanded number of incremental rotations that is likely to be attributable to the tolerance, inaccuracy, or other variations exhibited by the motor position sensor 500, 910. For example, the threshold value may be equal to about 5% of the commanded number of incremental rotations. Thus, when the measured number of incremental rotations for the rotor 530 is within 5% of the commanded number of incremental rotations, the motor control module 902 determines that the commanded rewind of the gear assembly 236, 936 in the negative delivery direction was achieved and that the gear assembly 236, 936 is in the reset state depicted in FIG. 8.

In response to determining that the desired rewinding of the gear assembly was not achieved, the control process 1000 pauses operation of the motor for a delay period before repeating operation of the motor to achieve the desired amount of rewinding (tasks 1004, 1012). In this regard, the delay period is chosen to be an amount of time that allows the energy source 930 to recover from the continuous operation of the PWM module 904 and motor driver module 906 that was previously undertaken to drive the motor 232, 908 the commanded number of motor steps in the negative delivery. Thereafter, the control module 902 may determine the difference between the measured number of incremental rotations and the commanded number of incremental rotations of the rotor, convert the difference into a number of motor steps, and thereafter operate the PWM module 904 and/or motor driver module 906 to achieve that number of motor steps in the negative delivery direction. For example, the control module 902 may signal or otherwise command the PWM module 904 to increase the duty cycle (e.g., to provide PWM signals having a duty cycle greater than 70%) to ensure that the desired amount of rewinding of the gear assembly 236, 936 is achieved.

In exemplary embodiments, after rewinding the gear assembly to the reset state, the control process 1000 continues by determining whether the axial force measured by the force sensor in the gear assembly is less than a threshold force indicative of a reservoir being absent from the fluid infusion device (task 1014). In this regard, the control module 902 confirms that the force sensor 440, 940 is functioning properly and/or that there is no reservoir present in the fluid infusion device 200 by obtaining the axial force measured by the force sensor 440, 940 and determining whether the measured axial force is less than the threshold force. The threshold force may be chosen to be a fraction of the nominal force measured by the force sensor 440, 940 during normal operation of the infusion device 200 when the reservoir 206 is present and seated within the infusion device 200. For example, in accordance with one embodiment, the threshold force value may be chosen to be in the range of about 20% to about 25% of the nominal force measured by the force sensor 440, 940 during normal operation when the reservoir 206 present and seated in the infusion device 200 and there is no fluid path occlusion. In exemplary embodiments, the threshold force value is less than an amount used to indicate the presence of a reservoir in the durable housing 202 (e.g., the reservoir seating force threshold). When the axial force measured by the force sensor in the gear assembly greater than the threshold force value, the control process 1000 continues by generating or otherwise providing an indication of a potential anomalous condition (task 1016). For example, the control module 902 may signal or otherwise provide notification to the pump control system 920 that there is a potential anomaly within gear assembly 236, 936 and/or the force sensor 440, 940, and in turn, the pump control system 920 may generate or otherwise provide some sort of auditory and/or visual notification to the user that there is a potential anomaly within the infusion device 200. Additionally, the motor control module 902 and/or the pump control system 920 may take one or more remedial actions to mitigate the potential anomaly, for example, by using modified control schemes that do not rely on the force sensor 440, 940 or otherwise augment the force measurements obtained by the force sensor 440, 940 to account for any potential anomalies.

Figure 11:
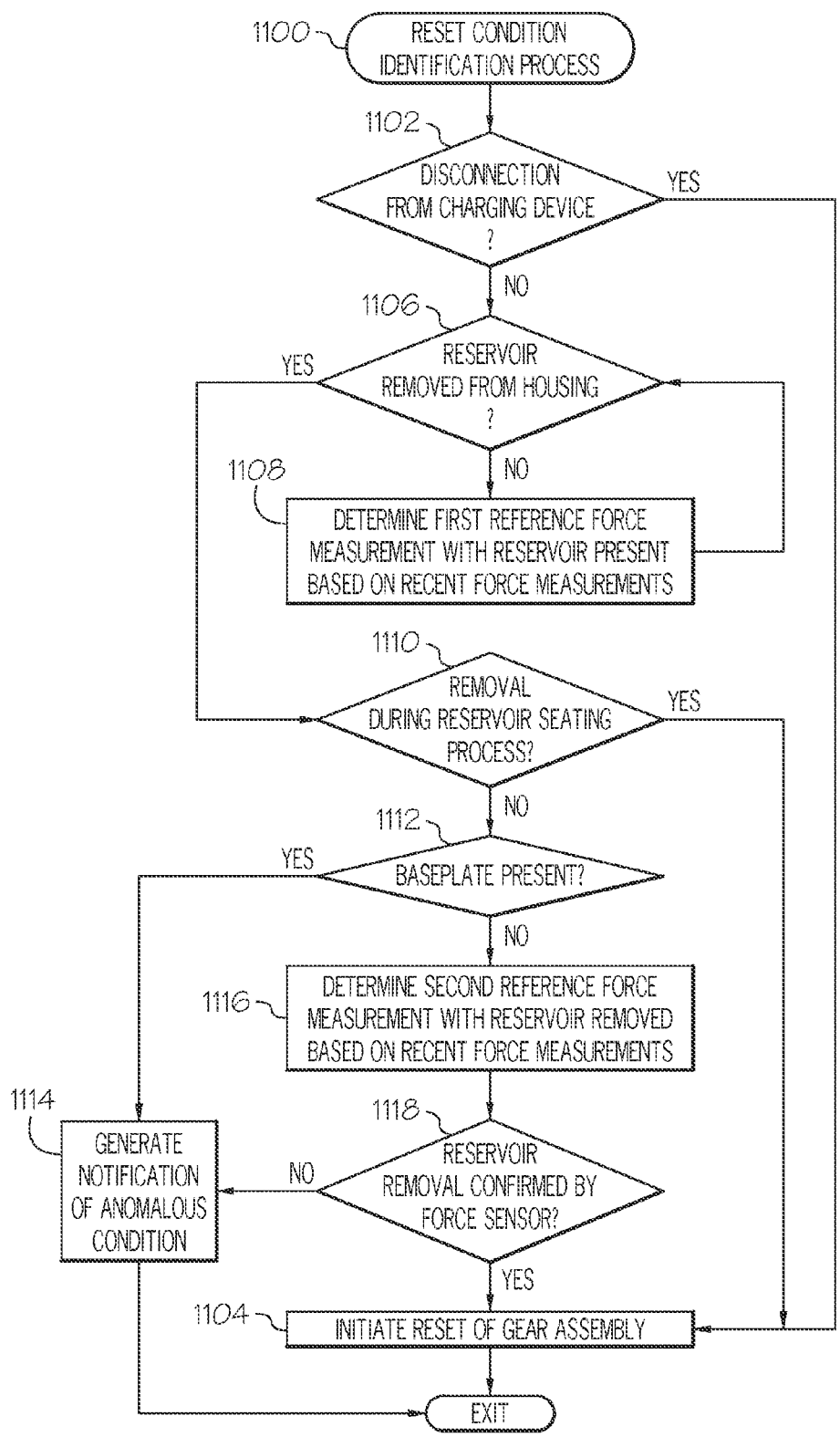
FIG. 11 is a flow diagram of an exemplary reset condition identification process suitable for use with the control process of FIG. 10.

FIG. 11 depicts an exemplary reset condition identification process 1100 suitable for implementation by a control system in a fluid infusion device in conjunction with the control process 1000 of FIG. 10. The various tasks performed in connection with the reset condition identification process 1100 may be performed by software, hardware, firmware, or any combination thereof. For illustrative purposes, the following description refers to elements mentioned above in connection with FIGS. 1-9. In practice, portions of the reset condition identification process 1100 may be performed by different elements of the infusion device 900, such as, for example, the control module 902, the PWM module 904, the motor driver module 906, the motor 908, the position sensor 910, and/or the sensing arrangement 960. It should be appreciated that the reset condition identification process 1100 may include any number of additional or alternative tasks, the tasks need not be performed in the illustrated order and/or the tasks may be performed concurrently, and/or the reset condition identification process 1100 may be incorporated into a more comprehensive procedure or process having additional functionality not described in detail herein. Moreover, one or more of the tasks shown and described in the context of FIG. 11 could be omitted from a practical embodiment of the reset condition identification process 1100 as long as the intended overall functionality remains intact.

In exemplary embodiments, the reset condition identification process 1100 begins by detecting or otherwise identifying whether durable housing of the fluid infusion device is being removed or otherwise disconnected from a charging device (task 1102). For example, the durable housing 202 may be electrically connected to a charging device to charge an internal energy source or battery, such as energy source 930. The sensing arrangement 960 may include a sensing element adapted to detect or otherwise identify when the durable housing 202 is connected to and/or disconnected from the charging device. For example, the charging device may periodically emit a signal or pulse that is detected by the sensing element, thereby indicating that the durable housing 202 is connected to the charging device. When the sensing element fails to detect the pulse signal for an amount of time that is greater than the period of the pulse signal, the sensing element may provide an indication to the control module 902 that the durable housing 202 is no longer connected to the charging device. In exemplary embodiments, in response to detecting the durable housing being disconnected from the charging device, the reset condition identification process 1100 identifies a reset condition and automatically initiates resetting the gear assembly to its reset state (task 1104). Accordingly, when the control module 902 identifies the durable housing has been disconnected from the charging device, the control module 902 identifies a reset condition and automatically operates the motor 908 to rewind the gear assembly 936 (tasks 1002, 1004), as described above in the context of FIG. 9. In this regard, the durable housing and/or the charging device may be configured so that the durable housing cannot be connected to the charging device while a reservoir is present or otherwise seated in the durable housing. Thus, the gear assembly is configured in a reset state so that the durable housing is capable of accommodating insertion of a reservoir whenever the durable housing is removed from the charging device.

If the reset condition identification process 1100 determines that the durable housing of the infusion device is not being disconnected from a charging device, the reset condition identification process 1100 continues by detecting or otherwise identifying whether a fluid reservoir has been removed from the durable housing (task 1106). For example, as described above in the context of FIG. 10, the sensing arrangement 960 may include a sensing element adapted to detect or otherwise identify when the reservoir 206 is seated or otherwise positioned within a corresponding voided region of the durable housing 202. When the sensing element fails to detect the reservoir 206, the sensing element may provide an indication to the control module 902 that the reservoir 206 is no longer present within the durable housing 202. In the illustrated embodiment, while the reservoir is maintained in the durable housing, the reset condition identification process 1100 continues by determining a first reference force measurement corresponding to the axial force measured by the force sensor integrated with the gear assembly when the reservoir is present using the most recently obtained force measurements (task 1108). In exemplary embodiments, the control module 902 obtains a current force measurement from the force sensor 440, 940 and calculates the first reference force measurement as a moving average of the current force measurement and the most recently obtained force measurements that precede the current force measurement. For example, in one embodiment, the control module 902 determines the first reference force measurement as a moving average of the four most recently obtained force measurements from the force sensor 440, 940. Accordingly, the first reference force measurement may be updated for each time the reset condition identification process 1100 is performed.

In response to detecting the reservoir being removed from the infusion device, the reset condition identification process 1100 continues by determining whether the reservoir was removed during execution of a reservoir seating process and automatically initiating reset of the gear assembly to its reset state when the reservoir removal was detected during execution of a reservoir seating process (tasks 1104, 1110). In this regard, in exemplary embodiments, the control module 902 performs a reservoir seating process to prepare the infusion device 200, 900 and/or the control system 901 for delivering fluid to the user upon detecting the reservoir 206 being inserted into the durable housing 202. The reservoir seating process may be similar to those described in U.S. patent application Ser. No. 13/528,258 or U.S. patent application Ser. No. 12/976,619, which are incorporated by reference herein. For example, as part of the reservoir seating process, the control module 902 may operate the motor 232, 908 to remove slack from the gear assembly 236, 936 by providing signals or commands to the PWM module 904 and/or the motor driver module 906 to operate the motor 908 in the positive delivery direction to axially displace the worm gear 242 and/or axle 442 in the delivery direction 450 into contact with the force sensor 440, 940 but with little or no displacement of the shaft 224 in the delivery direction 250. When the reservoir is removed during the reservoir seating process, the removal may be temporary and the user may subsequently attempt to reinsert the reservoir within a relatively short period of time, and thus, it may be desirable to rewind the gear assembly as soon as possible when the reservoir seating process is interrupted to readily accommodate subsequent reinsertion of the reservoir. Accordingly, when the removal of the reservoir 206 is identified by the control module 902 during execution of the reservoir seating process, the control module 902 ceases executing the reservoir seating process and automatically begins operating the motor 908 to rewind the gear assembly 936 to a reset state (e.g., task 1004).

If a reservoir seating process is not being performed when the reservoir removal is detected, the reset condition identification process 1100 continues by determining whether the base plate is joined to the durable housing and generating a notification of an anomalous condition when the baseplate is detected (tasks 1112, 1114). For example, the sensing arrangement 960 may include a sensing element adapted to detect or otherwise identify when the durable housing 202 is connected to or otherwise joined to the base plate 204. When the reservoir removal is detected while the sensing element detects the durable housing 202 is joined to the base plate 204, the control module 902 generates or otherwise provides a notification of an anomalous condition to the pump control system 920 because removal of the reservoir should not occur while the durable housing 202 is joined to the base plate 204. In response, the pump control system 920 may generate or otherwise provide an auditory and/or visual alert that notifies the user of a need to inspect the durable housing 202 and/or base plate 204 to ensure that the reservoir 206 has not become inadvertently dislodged or otherwise unseated within the infusion device 200.

Still referring to FIG. 11, in exemplary embodiments, after confirming that the durable housing is no longer joined to the base plate, the reset condition identification process 1100 continues by determining a second reference force measurement corresponding to the axial force measured by the force sensor integrated with the gear assembly when the reservoir is removed and confirming that the second reference force measurement indicates removal of the reservoir before initiating reset of the gear assembly (tasks 1116, 1118). In this manner, the control module 902 confirms that the force sensor 440, 940 is functioning in an expected manner by confirming that the current force measurements are not consistent with the reservoir being seated or otherwise in engagement with the gear assembly 236, 936. In exemplary embodiments, the control module 902 obtains a number of force measurements from the force sensor 440, 940 with the reservoir removed and calculates the second reference force measurement by averaging those measurements. For example, in one embodiment, the control module 902 determines the second reference force measurement by obtaining sixteen force measurements from the force sensor 440, 940 and averaging those measurements. In exemplary embodiments, the control module 902 confirms that the second reference force measurement is less than a fraction of the first reference force measurement. For example, in one embodiment, the control module 902 determines whether the second reference force measurement is less than the 70% of the first reference force measurement. When the second reference force measurement is not less than the first reference force measurement (or a factor thereof), the reset condition identification process 1100 generates or otherwise provides a notification of an anomalous condition to the pump control system to indicate the discrepancy in the force sensor measurements (task 1114). Conversely, when the second reference force measurement is consistent with the reservoir being absent from the infusion device, the reset condition identification process 1100 confirms the force sensor is functioning in an expected manner and initiates reset of the gear assembly (task 1104), as described above.

Figure 12:
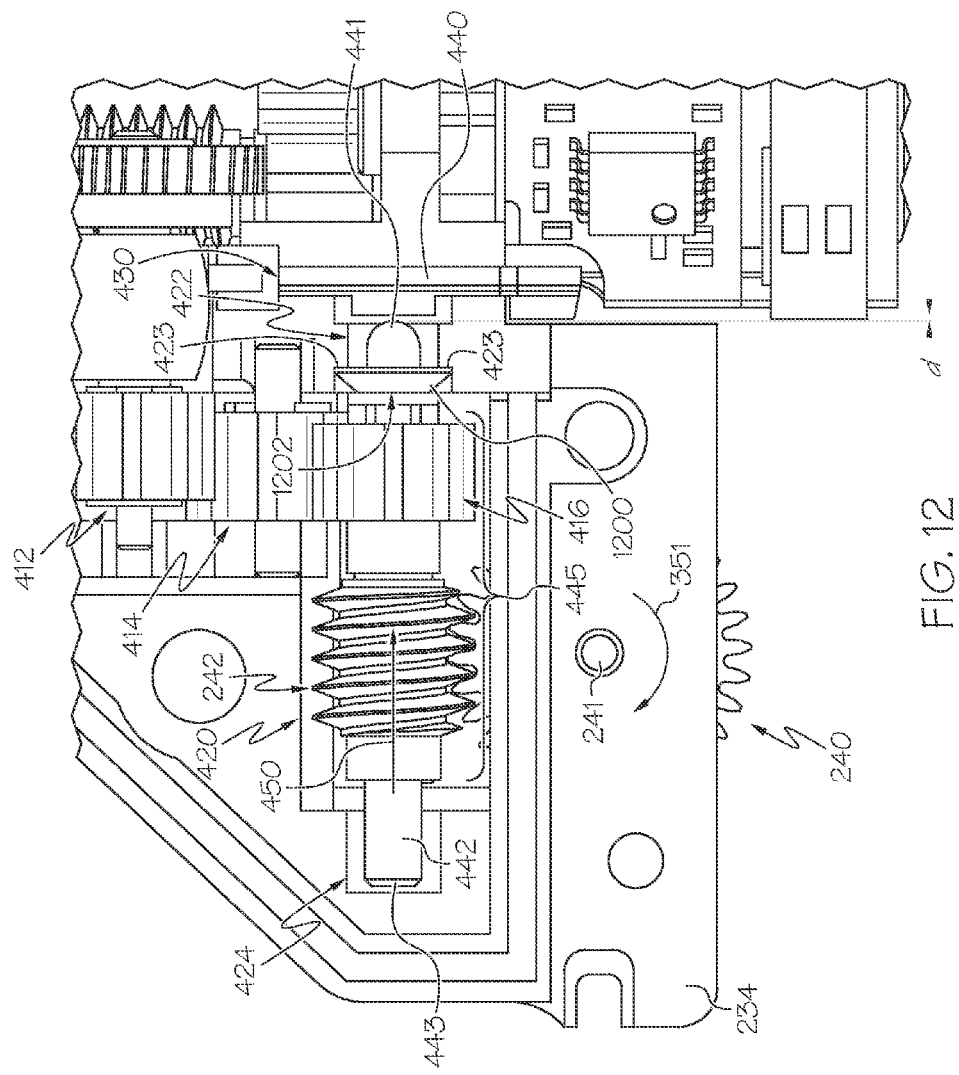
FIG. 12 is a plan view illustrating the gear assembly in a reset state with the fluid reservoir removed from the durable housing of FIG. 3 in accordance with another embodiment.
Figure 13:
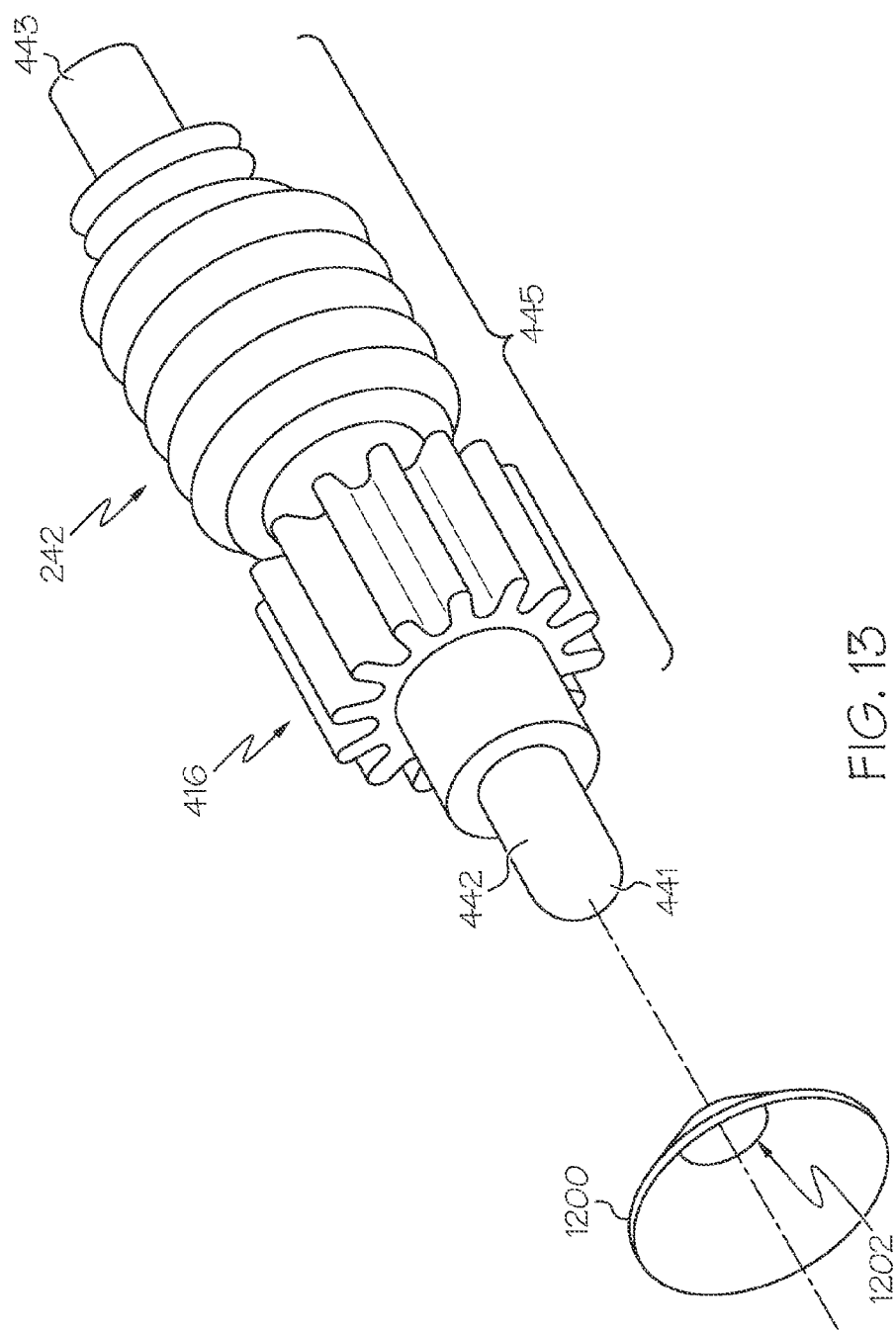
FIG. 13 is an exploded perspective view illustrating the relationship between the axle of the worm gear of the gear assembly and the mechanical element of FIG. 12.

Turning now to FIGS. 12-13, and with reference to FIGS. 1-6, in accordance with one or more alternative embodiments, the fluid infusion device 200 includes a mechanical element 1200 that applies a force that biases the gear assembly 236 to a reset state when the reservoir 206 is removed from the durable housing 202 and thereby provides, to the pinion gear 238, rotational freedom in the negative delivery direction 351. In the illustrated embodiment, the mechanical element 1200 is realized as a spring-loaded element disposed within the voided region 420 of the frame structure 234 proximate the opening 422 to apply force to the axle 442 of the worm gear 242 in the direction opposite the axial delivery direction 450. For example, the mechanical element 1200 may be realized as a compression spring (e.g., a conical coil spring) having a hollow interior 1202 with an inner circumference greater than an outer circumference of an end 441 of the axle 442, so that the end 441 of the axle 442 may be inserted through the hollow interior 1202 of the mechanical element 1200 as well as the opening 422, such that the mechanical element 1200 circumscribes that end portion of the axle 442. The outer circumference of the mechanical element 1200 is greater than the circumference of the opening 422, so that the lip portion 423 of the frame structure 234 that defines the circumference of the opening 422 restricts, restrains, or otherwise prevents mechanical element 1200 from being displaced in the axial delivery direction 450. The outer circumference of the central portion 445 of the axle 442 is greater than the circumference of the hollow interior 1202 so that only the end portion of the axle 442 may be inserted through the hollow interior 1202 while displacement of the central portion 445 of the axle 442 (e.g., the worm gear 242 and spur gear 412) is inhibited or otherwise resisted by the mechanical element 1200. In this manner, the mechanical element 1200 is disposed between the lip portion 423 of the frame structure 234 and the central portion 445 of the axle 442 to apply a force to the axle 442 that resists displacement of the axle 442, and thereby worm gear 242, in the axial delivery direction 450.

In exemplary embodiments, the mechanical element 1200 is configured to apply a force in the negative axial delivery direction that is greater than the force attributable to static friction in the gear assembly 236 to that the mechanical element 1200 displaces the axle 442 in the negative delivery direction in the absence of a force applied to the worm gear 242 in the axial delivery direction 450. In this regard, when the reservoir 206 is removed from the infusion device 200, the teeth 225 of the shaft 224 of the reservoir 206 no longer apply force to the teeth 239 of the pinion gear 238, and thus, the spur gear 240 does not resist displacement of the worm gear 242 in the negative delivery direction. Accordingly, when the reservoir 206 is not present, the mechanical element 1200 biases the end 441 of the axle 442 away from the force sensor 440 (e.g., by a distance d). In this regard, when the reservoir 206 is removed, the force applied by the mechanical element 1200 displaces the worm gear 242 in the negative delivery direction. Displacement of the worm gear 242 in the negative delivery direction rotates the pinion gear 238 in the delivery rotational direction, which, in turn, subsequently provides the pinion gear 238 with rotational freedom in the negative delivery rotational direction 351 by increasing the distance between the end 441 of the axle 442 and the force sensor 440 and/or lip portion 423. Accordingly, when the reservoir 206 is reinserted into the infusion device 200, the pinion gear 238 is capable of rotating in the negative delivery rotational direction 351 by displacing the worm gear 242 in the axial delivery direction 450 (e.g., via axle 241 and spur gear 240). In this regard, in exemplary embodiments, the force applied by the mechanical element 1200 in the negative axial delivery direction may be chosen to be less than a nominal amount of force required to displace the shaft 224 and/or plunger 222 of the reservoir 206 in the delivery direction 250, so that the pinion gear 238 rotates in the negative delivery rotational direction 351 to accommodate insertion of the reservoir 206 without delivering fluid from the reservoir 206 to the user.

Depending on the embodiment, the mechanical element 1200 may be configured to provide a desired amount of rotational freedom to the pinion gear 238. For example, in some embodiments, the mechanical element 1200 may be realized as a compression spring having a length configured to displace the axle 442 of the worm gear 242 in the negative delivery direction until the end 443 of the axle 442 contacts the frame structure 234 at the end of the cutout portion 424 to provide a maximum amount of rotational freedom to the pinion gear 238 in the negative delivery direction 351 (or alternatively, a minimum amount of rotational freedom in the delivery direction 350). In other embodiments, the mechanical element 1200 may be configured to provide an equal amount of rotational freedom to the pinion gear 238 in both the negative delivery direction 351 and the positive delivery direction 350, for example, by making the axle 442 equidistant from the restraining features at either end of the axle 442. For example, the mechanical element 1200 may be realized as a compression spring having a length configured so that the distance between the end 443 of the axle 442 and the frame structure 234 at the end of the cutout portion 424 is substantially equal to the distance between the opposing end 441 of the axle 442 and the force sensor 440 (e.g., distance d). It should be appreciated that there are numerous potential configurations for the mechanical element 1200 that may be utilized in a practical embodiment which will not be exhaustively described herein.

Figure 14:
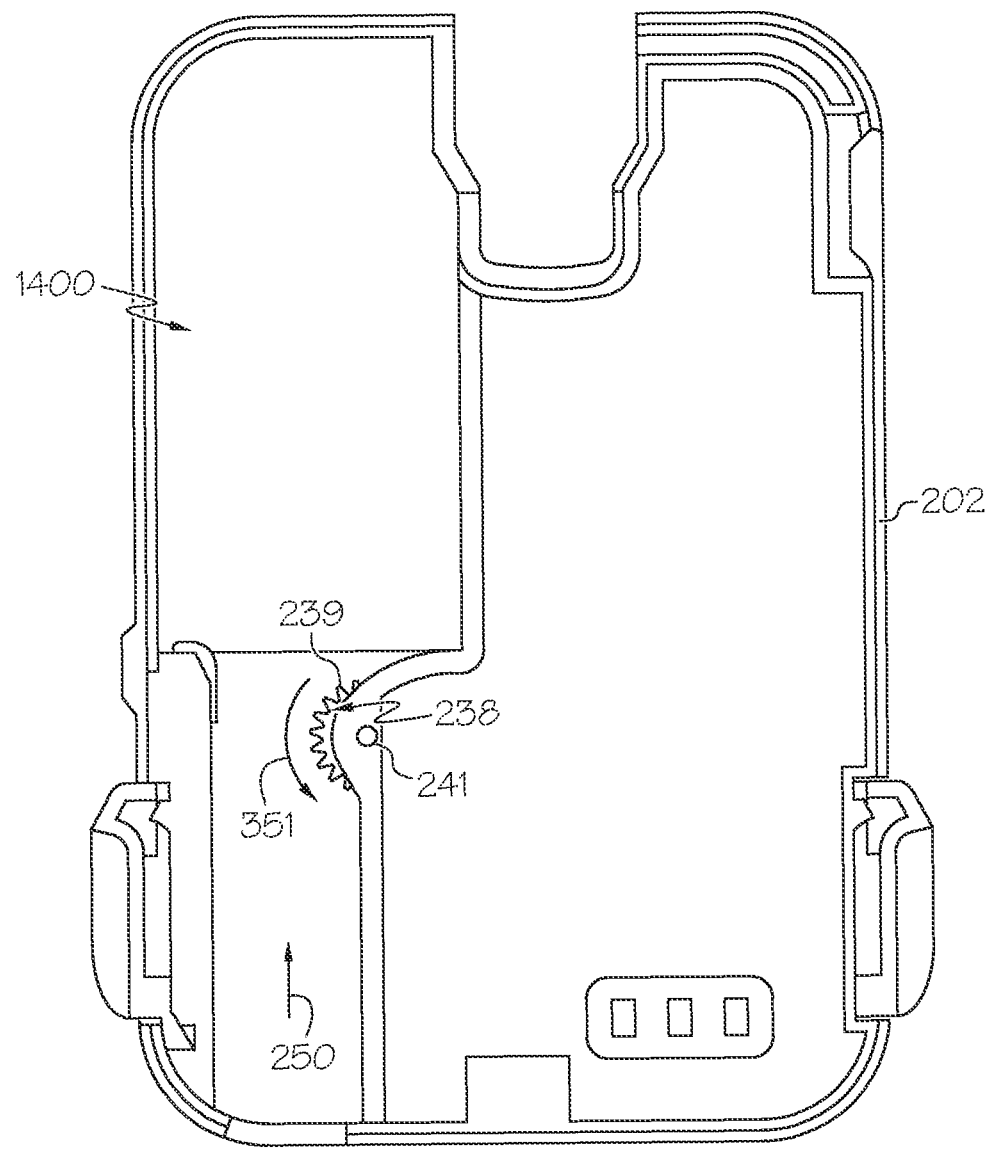
FIG. 14 is a plan view illustrating the rotational freedom of the gear that engages the shaft of the fluid reservoir when the fluid reservoir is removed from the durable housing of FIG. 3.

Turning now to FIG. 14, and with reference to FIGS. 1-13, by virtue of the subject matter described herein, when there is no reservoir 206 inserted in the corresponding voided region 1400 of the durable housing 202, the pinion gear 238 that is positioned proximate the voided region 1400 to engage the shaft 224 of the reservoir 206 exhibits rotational freedom in a direction 351 opposite the delivery direction 250, 350. Thus, when the reservoir 206 is inserted in the voided region 1400, the teeth 225 of the shaft 224 of the reservoir 206 may engage the exposed teeth 239 of the pinion gear 238 and rotate the pinion gear 238 in the negative delivery direction 351 about its axle 241, thereby reducing the likelihood of inadvertent displacement of the shaft 224 in the delivery direction 250 that could otherwise be caused by misalignment of the shaft teeth 225 with respect to the pinion gear teeth 239. Thereafter, a reservoir seating process may be performed to remove any slack in the gear assembly 236 (e.g., by axially displacing the worm gear 242 and/or axle 442 in the axial delivery direction 450) to ensure subsequent delivery of fluid from the reservoir 206 is achieved in the desired manner.

The foregoing description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the herein for the purpose of reference only, and thus is not intended to be limiting. For example, terms such as "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion device comprising:
 a housing to receive a shaft coupled to a plunger disposed in a reservoir;
 a gear assembly including a first gear to engage the shaft and a worm gear coupled to the first gear, the first gear having rotational freedom in a direction opposite a delivery direction, the worm gear exhibiting axial displacement in a first direction in response to rotation of the first gear in the direction opposite the delivery direction;
 a force sensor aligned with an axle of the worm gear;
 a motor having a rotor coupled to the gear assembly; and
 a control module coupled to the motor to operate the motor to displace the axle of the worm gear in a second direction opposite the first direction and away from the force sensor in response to the reset condition.

2. The infusion device of claim 1, wherein the first gear comprises a pinion gear including teeth configured to mate with corresponding teeth of the shaft.

3. The infusion device of claim 1, further comprising a frame structure including a voided region having an axle of the worm gear disposed therein, wherein a length of the voided region is greater than a length of the axle.

4. The infusion device of claim 1, wherein the axial displacement in the first direction is towards the force sensor.

5. The infusion device of claim 4, further comprising a frame structure including a voided region having the axle of the worm gear disposed therein, the voided region including an opening aligned with the force sensor, an end of the axle extending through the opening.

6. The infusion device of claim 1, further comprising a frame structure to support the worm gear, the frame structure including a voided region having an axle of the worm gear disposed therein, wherein the control module operates the motor to displace the axle of the worm gear in the second direction in response to the reset condition.

7. The infusion device of claim 6, wherein the control module operates the motor to displace the worm gear in the second direction until the frame structure restricts further displacement of the worm gear in the second direction.

8. The infusion device of claim 7, wherein:
 a length of the voided region is greater than a length of the axle; and
 the control module operates the motor to displace the worm gear in the second direction so that a first end of the axle contacts the frame structure in response to the reset condition.

9. The infusion device of claim 8, wherein the voided region includes an opening having an opposing end of the axle disposed therein.

10. The infusion device of claim 9, wherein the force sensor is aligned with the opening, the displacement of the worm gear in the second direction increasing a distance between the opposing end of the axle and the force sensor.

11. The infusion device of claim 1, wherein the control module operates the motor to achieve a fixed amount of rotation of the rotor in a negative delivery direction.

12. The infusion device of claim 11, wherein the fixed amount of rotation provides slack in the gear assembly, the slack resulting in the rotational freedom in the negative delivery direction.

13. The infusion device of claim 1, wherein the control module identifies the reset condition in response to the reservoir being removed from the housing.

14. The infusion device of claim 1, further comprising a mechanical element coupled to the first gear, the mechanical element applying force to rotate the first gear in the direction opposite the delivery direction.

15. The infusion device of claim 14, wherein rotation of the first gear in the direction opposite the delivery direction results in the rotational freedom.

16. The infusion device of claim 14, wherein the mechanical element applies the force to an axle of the worm gear in a second direction opposite the first direction.

17. The infusion device of claim 16, further comprising a frame structure including a voided region having the axle of the worm gear disposed therein, wherein:
 the mechanical element is disposed between a central portion of the axle and the frame structure; and
 the frame structure prevents displacement of the mechanical element in the first direction.

18. An infusion device comprising:
 a housing to receive a shaft coupled to a plunger disposed in a reservoir;
 a gear assembly including a first gear to engage the shaft and a worm gear coupled to the first gear, the worm gear exhibiting axial displacement in a first direction in response to rotation of the first gear in the direction opposite the delivery direction;
 a force sensor aligned with an axle of the worm gear;
 a motor having a rotor coupled to the gear assembly; and
 a control module coupled to the motor to operate the motor to provide rotational freedom for the first gear in a direction opposite a delivery direction for the plunger by operating the motor to displace the axle of the worm gear in a second direction opposite the first direction and away from the force sensor in response to a reset condition.

19. The infusion device of claim 18, wherein the control module identifies the reset condition in response to removal of the reservoir from the housing.

20. An infusion device comprising:
 a housing to receive a shaft coupled to a plunger of a reservoir;
 a gear assembly including a first gear to engage the shaft and a worm gear coupled to the first gear, the worm gear exhibiting axial displacement in a first direction in response to rotation of the first gear in the direction opposite the delivery direction;
 a mechanical element coupled to the first gear, the mechanical element applying force to an axle of the worm gear in a second direction opposite the first direction resulting in the first gear exhibiting rotational freedom in a direction opposite a delivery direction of the plunger;
 a force sensor aligned with an axle of the worm gear;
 a motor having a rotor coupled to the gear assembly; and a control module coupled to the motor to operate the motor to displace the axle of the worm gear in the second direction and away from the force sensor in response to the reset condition.

21. The infusion device of claim 20, further comprising a frame structure to support the worm gear, wherein the mechanical element is disposed between a central portion of the axle and the frame structure, the frame structure preventing displacement of the mechanical element in the first direction.

22. The infusion device of claim 21, wherein the mechanical element has a hollow interior circumscribing an end portion of the axle.

23. The infusion device of claim 21, wherein the mechanical element comprises a compression spring.

* * * * *